(12) United States Patent
Rapaport

(10) Patent No.: US 10,228,238 B2
(45) Date of Patent: Mar. 12, 2019

(54) METHODS FOR EVALUATING GEMSTONE SHAPE

(71) Applicant: Martin Rapaport, Las Vegas, NV (US)

(72) Inventor: Martin Rapaport, Las Vegas, NV (US)

(*) Notice: Subject to any disclaimer, the term of this patent is extended or adjusted under 35 U.S.C. 154(b) by 427 days.

(21) Appl. No.: 14/775,152

(22) PCT Filed: Mar. 13, 2014

(86) PCT No.: PCT/IL2014/050287
§ 371 (c)(1),
(2) Date: Sep. 11, 2015

(87) PCT Pub. No.: WO2014/141282
PCT Pub. Date: Sep. 18, 2014

(65) Prior Publication Data
US 2016/0033261 A1    Feb. 4, 2016

Related U.S. Application Data

(60) Provisional application No. 61/784,443, filed on Mar. 14, 2013.

(51) Int. Cl.
| | |
|---|---|
| *G06T 7/12* | (2017.01) |
| *G06T 7/33* | (2017.01) |
| *G06T 7/68* | (2017.01) |
| *G01B 11/24* | (2006.01) |
| *G01N 21/87* | (2006.01) |
| *G06Q 30/02* | (2012.01) |

(Continued)

(52) U.S. Cl.
CPC .............. *G01B 11/24* (2013.01); *G01N 21/87* (2013.01); *G06Q 30/0283* (2013.01); *G06T 7/12* (2017.01); *G06T 7/337* (2017.01); *G06T 7/536* (2017.01); *G06T 7/68* (2017.01); *H04N 5/374* (2013.01); *G06T 2207/10028* (2013.01); *G06T 2207/10148* (2013.01); *G06T 2207/30244* (2013.01)

(58) Field of Classification Search
CPC .......... G01B 11/24; G06T 7/536; G06T 7/12; G06T 7/337; G06T 7/68; G06T 2207/30244; G06T 2207/10028; G06T 2207/10148; H04N 5/374; G06Q 30/0283; G01N 21/87
See application file for complete search history.

(56) References Cited

U.S. PATENT DOCUMENTS

| | | | |
|---|---|---|---|
| 4,417,564 A * | 11/1983 | Lawrence ............... | B24B 9/162 125/30.01 |
| 5,966,673 A | 10/1999 | Shannon, Sr. | |

(Continued)

FOREIGN PATENT DOCUMENTS

| | | |
|---|---|---|
| EP | 1319942 A1 | 6/2003 |
| WO | 2014/141282 A1 | 9/2014 |

OTHER PUBLICATIONS

International Search Report and Written Opinion both dated Jul. 9, 2014; PCT/IL2014/050287.

(Continued)

*Primary Examiner* — Joseph G Ustaris
*Assistant Examiner* — Jill D Sechser
(74) *Attorney, Agent, or Firm* — Ladas & Parry LLP

(57) ABSTRACT

This disclosure relates to methods of evaluating the shape of a gemstone, such as a diamond, ruby, emerald, or sapphire. Also provided are methods of identifying gemstone shape.

16 Claims, 43 Drawing Sheets

(51) Int. Cl.
*G06T 7/536* (2017.01)
*H04N 5/374* (2011.01)

(56) References Cited

U.S. PATENT DOCUMENTS

| | | | |
|---|---|---|---|
| 6,020,954 A * | 2/2000 | Aggarwal | G01N 21/87 356/30 |
| 6,239,867 B1 | 5/2001 | Aggarwal | |
| 6,567,156 B1 | 5/2003 | Kerner | |
| 8,046,274 B2 | 10/2011 | Sevdermish | |
| 2002/0052170 A1 | 5/2002 | Holloway | |
| 2003/0065586 A1* | 4/2003 | Shaftel | G06Q 30/06 705/27.1 |
| 2004/0068417 A1 | 4/2004 | Sevdermish | |
| 2005/0036132 A1* | 2/2005 | Lapa | G01N 21/87 356/30 |
| 2005/0149369 A1* | 7/2005 | Sevdermish | G01N 21/87 705/306 |
| 2006/0074588 A1 | 4/2006 | Blodgett et al. | |
| 2006/0190292 A1 | 8/2006 | Reinitz et al. | |
| 2010/0092067 A1* | 4/2010 | Ellawand | G01N 21/41 382/141 |
| 2011/0310246 A1 | 12/2011 | Hornabrook et al. | |

OTHER PUBLICATIONS

International Preliminary Report on Patentability dated Sep. 15, 2015; PCT/IL2014/050287.
U.S. Appl. No. 61/784,443, filed Mar. 14, 2013.
Extended European Search Report dated Oct. 7, 2016; Appln. No. 14762335.9-1504/2972249 PCT/IL2014050287.

* cited by examiner

METHODS FOR EVALUATING GEMSTONE SHAPE

CROSS REFERENCE TO RELATED APPLICATIONS

Benefit is claimed to U.S. Provisional Patent Application No. 61/784,443, filed on Mar. 14, 2013; the contents of which are incorporated by reference in their entirety.

FIELD

This disclosure relates to methods of evaluating the shape of a gemstone, such as a diamond, ruby, emerald, or sapphire. Also provided are methods of identifying gemstone shape.

BACKGROUND

Gemstones, such as diamonds, rubies, emeralds, or sapphires, are valued by observation and measurement of numerous physical characteristics. Perhaps best known are long-established criteria for valuing diamonds. Cut diamonds are valued based on differences in shape, size range, cut, clarity, color, polish, symmetry, fluorescence, finish and light performance. Rough diamonds are valued based on differences in shape, size range, color, clarity, and cut estimate. Diamond value is often also based on the source and reputation of the gemological laboratory providing the grading report for an individual stone.

A variety of gemological laboratories (e.g. American Gem Society (AGS), the Gemological Institute of America (GIA); and Rapaport Laboratories (RAP)) produce grading reports which provide the results of diamond appraisals. Standard grading reports typically indicate the "shape" or "cut" of an appraised gemstone. However standard grading reports are silent regarding how closely the gemstone resembles its purported shape.

Thus a continuing need exists for methods for evaluating the shape of a gemstone.

SUMMARY

Disclosed herein are methods for evaluating a gemstone shape. The disclosed methods include obtaining a test gem image, comparing the overall shape (or an aspect thereof) of the test gem in the test gem image to one or more ("at least one") reference representation of the test gem shape type (a "reference shape"), and determining the differences between the test gem shape and the one or more reference shapes. In some embodiments, the disclosed methods focus the comparison of the test gem and reference shapes on one or more facets or other particular aspects of the test gem and reference shapes. In those embodiments wherein the test gem shape is compared to more than one reference shape, the multiple reference shapes can be of the same shape from different perspectives, or multiple variations of the reference shape. Comparison to such multiple variations allows one of skill to determine the similarity of the test gem shape to the multiple variations and provide a shape grade based on the degree of similarity or difference between the test gem and the multiple variations.

Also disclosed herein are methods for identifying a gem shape. Such methods are useful in instances when a gem may share shape characteristics of multiple standard gem shapes. The described methods for identifying a gem shape are similar to the methods for evaluating gem shape, except instead of comparing the test gem to a single reference shape, the test gem is compared to multiple reference shapes (such as contained in a library of reference shapes). The test gem is identified as that shape with which it has the fewest differences (e.g. the shape that the test gem as the smallest non-overlapping area).

Computer-implemented embodiments of the described methods are also provided.

The foregoing and other objects, features, and advantages will become more apparent from the following detailed description, which proceeds with reference to the accompanying figures.

BRIEF DESCRIPTION OF THE DRAWINGS

FIG. 3 shows several views of an Asscher shape.

FIG. 4 shows several views of a Cushion shape.

FIG. 5 shows several views of an Emerald shape.

FIG. 6 shows several views of a Heart shape.

FIG. 7 shows several views of a Marquise shape.

FIG. 8 shows several views of an Oval shape.

FIG. 9 shows several views of a Pear shape.

FIG. 10 shows several views of an Princess shape.

FIG. 11 shows several views of a Radiant shape.

FIG. 12 shows several views of a Round shape.

DETAILED DESCRIPTION

I. Terms

Figure 1:
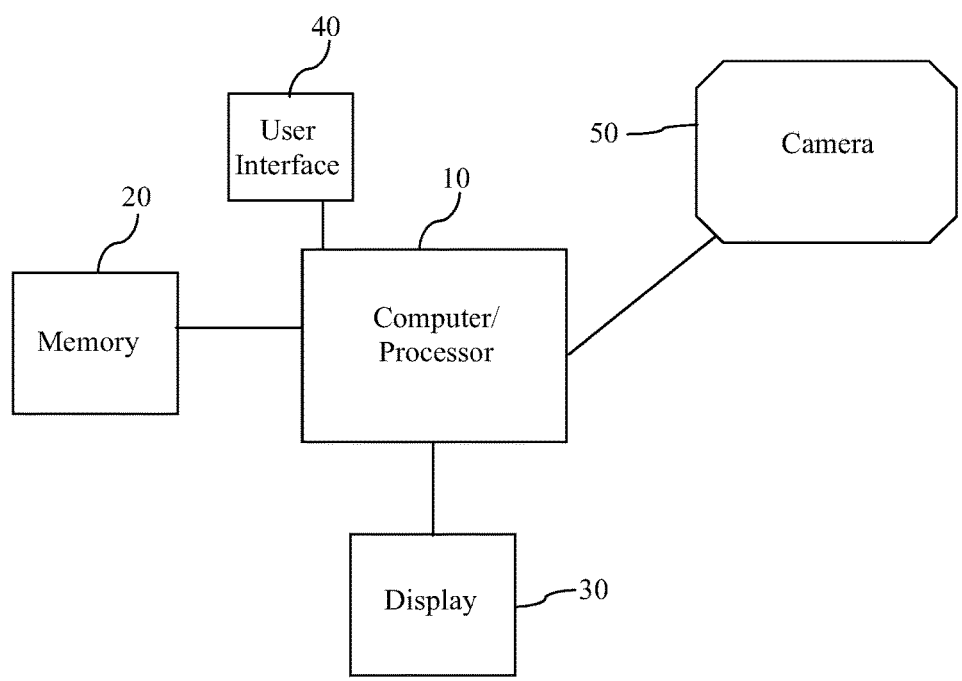
FIG. 1 shows an exemplary system for carrying out an embodiment of the methods described herein.

Unless otherwise explained, all technical used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict with the common understanding of terms used herein, the present specification, including explanations of terms, will control. In addition, all the materials, methods, and examples are illustrative and not intended to be limiting.

Adjusted weight: As disclosed herein, gemstones of specified shape and specified size (e.g. carat weight) have an ideal area. The disclosed methods of measuring shape conformity with a reference account for natural differences in size. Determination of adjusted weight accounts for gemstone size in determining the differences between a test diamond shape and a reference shape.

Obtaining an image: The process of acquiring and/or preparing an image. Obtaining an imaging encompasses image acquisition (e.g. imaging a test gem with a camera or a dedicated gem grading machine). Obtaining an image also encompasses preparing a previously-acquired image (e.g. scanning and digitizing a hard copy gem image; accessing from a memory a previously acquired image; and transferring a previously-acquired image to a film transparency).

Shape: Often used synonymously with "cut," gemstone shape describes a gemstone's overall appearance. Non-limiting examples of cut gemstone shapes include Heart, Emerald, Radiant, Rectangle, Princess, Marquise, S. French Marquise, Oval, Cushion, Pear, Pearmirage, French Pearmirage, French Pear, French Marquiz, Round, Asscher, and Trilliant. Non-limiting examples of rough gemstone shapes include: Octahedron, Sawable, Cleavage, Makable, Flat, Crystal, and Maacle.

Symmetry: In contrast to shape, symmetry relates to the orientation of individual facets of a cut gemstone, and the spatial relationship between facets, such as the alignment between facets.

III. Overview of Several Embodiments

Described herein is a method for evaluating the fidelity of a test gem shape to a reference shape, which includes obtaining an image of a test gem, such as a diamond, ruby, emerald, or sapphire, wherein the test gem image shows a test gem shape; comparing the test gem shape with at least one reference gem shape contained in at least one image showing the one or more reference gem shapes; determining differences between the test gem shape and the at least one reference gem shape; and assigning a shape grade to the test gem as a function of the determined differences, as an indication of the fidelity of the test gem shape to the reference gem shape or shapes.

In particular embodiments, the test gem image (and the image of the reference shape(s)) includes a two-dimensional image or a three-dimensional image. In other embodiments, the test gem image (and the image of the reference shape(s)) includes a top-down image, bottom-up image, perspective-view image or a side view image.

In some embodiments, the test gem and reference shapes are selected from the group consisting of Heart, Emerald, Radiant, Rectangle, Princess, Marquise, S. French Marquise, Oval, Cushion, Pear, Pearmirage, French Pearmirage, French Pear, French Marquiz, Round. Asscher, Trilliant, Octahedron, Sawable, Cleavage, Makable, Flat, Crystal, and Maacle, or a modification thereof. In other embodiments, the test gem and reference shapes are a shape having the dimensions of the shapes presented in FIGS. 3-12 and Tables 1-16.

In further embodiments, comparing the test gem shape with the reference gem shape involves overlaying the test gem image and the reference gem shape image. In yet further embodiments, determining the differences between the test gem shape and the reference gem shape includes calculating the non-overlapping area between the overlaid images. In still other embodiments, in place of determining the differences between the test gem shape and the reference gem shape, fidelity is determined by measuring the total percent overlap between the test gem shape and the reference gem shape.

In yet further embodiments, comparing the test gem shape with the reference gem shape includes comparing top-down views, bottom-up views, perspective views or side views of the test gem image and the reference gem shape image, comparing the shape of one or more facets of the test gem and the reference gem shape, or comparing the overall or partial curvature of the test gem shape with the reference gem shape.

In particular embodiments, prior to determining differences between the test gem shape and the reference gem shape, the image of the reference gem shape is adjusted to a size comparable to that of the test gem image.

In other embodiments, the dimensions of the test gem shape are measured prior to comparing the test gem shape with the reference gem shape.

In still further embodiments, the test gem and reference shape images show top views; and the method to additionally compares side-views, bottom views, or a portion thereof of the test gem and reference shape images.

Also described herein is a computer-implemented method for evaluating a gem shape including: obtaining an image of a test gem with a camera connected to a computer, wherein the test gem image shows a test gem shape; accessing from the computer memory, an image showing a reference gem shape; comparing the test gem shape with the reference gem shape; determining differences between the test gem shape and the reference gem shape; and displaying the differences between the test gem shape and the reference gem shape on a display.

In some examples, the test gem and reference shapes are selected from the group consisting of Heart, Emerald, Radiant, Rectangle, Princess, Marquise, S. French Marquise, Oval, Cushion, Pear, Pearmirage, French Pearmirage, French Pear, French Marquiz, Round. Asscher, Trilliant, Octahedron, Sawable, Cleavage, Makable, Flat, Crystal, and Maacle.

In particular embodiments, comparing the test gem shape with the reference gem shape includes displaying the test gem shape image and the reference gem shape image on the display and overlaying the images.

In other embodiments, prior to determining differences between the test gem shape and the reference gem shape, the reference gem shape image is adjusted to a size comparable to that of the test gem image.

Further described herein is a method for identifying a gem shape, including: obtaining an image of a test gem, wherein the test gem image shows a test gem shape; comparing the test gem shape with images of reference gem shapes; and determining the differences between the test gem shape and the reference gem shapes in the reference gem shape images, wherein the gem shape is identified as the reference gem shape having the fewest differences from the test gem shape. In particular embodiments of the methods for identifying a gem shape, a test shape is identified by determining the amount of similarity (by area or other spatial measurement) between the test gem shape and the reference gem shapes.

IV. Methods for Evaluating Gemstone Shape

Provided herein are methods for evaluating gemstone shape. The described methods include obtaining an image of a test gem of a particular shape (e.g. round); comparing the test gem shape with at least one reference of the particular gem shape, wherein the at least one reference can be variations of the same shape type; and determining differences between the test gem shape and the reference gem shape or shapes. In addition to evaluating overall gemstone shape to determine how well the test gem corresponds to the overall reference shape (or how well it corresponds to multiple variations of the same shape), particular embodiments of the described method relate to evaluating how closely one or more facets of the test gem shape correspond to analogous facets of the particular reference shape or one or more variations thereof under comparison. Other embodiments include evaluating the correspondence to a reference shape, multiple variations thereof, of particular profiles or other aspects of a test gem, such as the curvature of specific faces of the test gem shape.

In particular embodiments, the described methods are computer-implemented. An exemplary computer system for implementing the described methods is shown in FIG. 1. The described system requires a computer processor (10), memory (20), a display (30), a user interface (40), and a camera (50).

One of skill in the art will appreciate that myriad computer types are suitable for implementing the described method. However, the processor (10) must be sufficiently robust to receive a test gem image acquired from the camera (50) and compare the acquired test gem image to an image of a reference shape stored in the memory (20).

The memory (20) can be any type of computer memory common in the art, including "permanent" memory such as optical memory, solid state (flash) memory and the like, and "non-permanent" memory including all types of RAM memory. The memory can be internal to the computer system; local, external memory (e.g. stored on an optical drive externally-connected to the computer; or it can be part of an external database accessed by an intranet or internet network.

Similarly, the described display (30) can be any computer display, including a touch screen display, where applicable. Likewise, numerous user interfaces (40) are encompassed within the described system, including but not limited to, keyboard, mouse, touch screen, and voice recognition interfaces.

As described above, the camera (50) can be any device capable of imaging a test gem, such as, but not limited to, a still or video digital camera, or a dedicated diamond grading machine such as those produced and marketed by Sarin Technologies, Ltd. (Kfar Saba, Israel) and OGI Systems, Ltd. (Ramat Gan, Israel).

Figure 2:
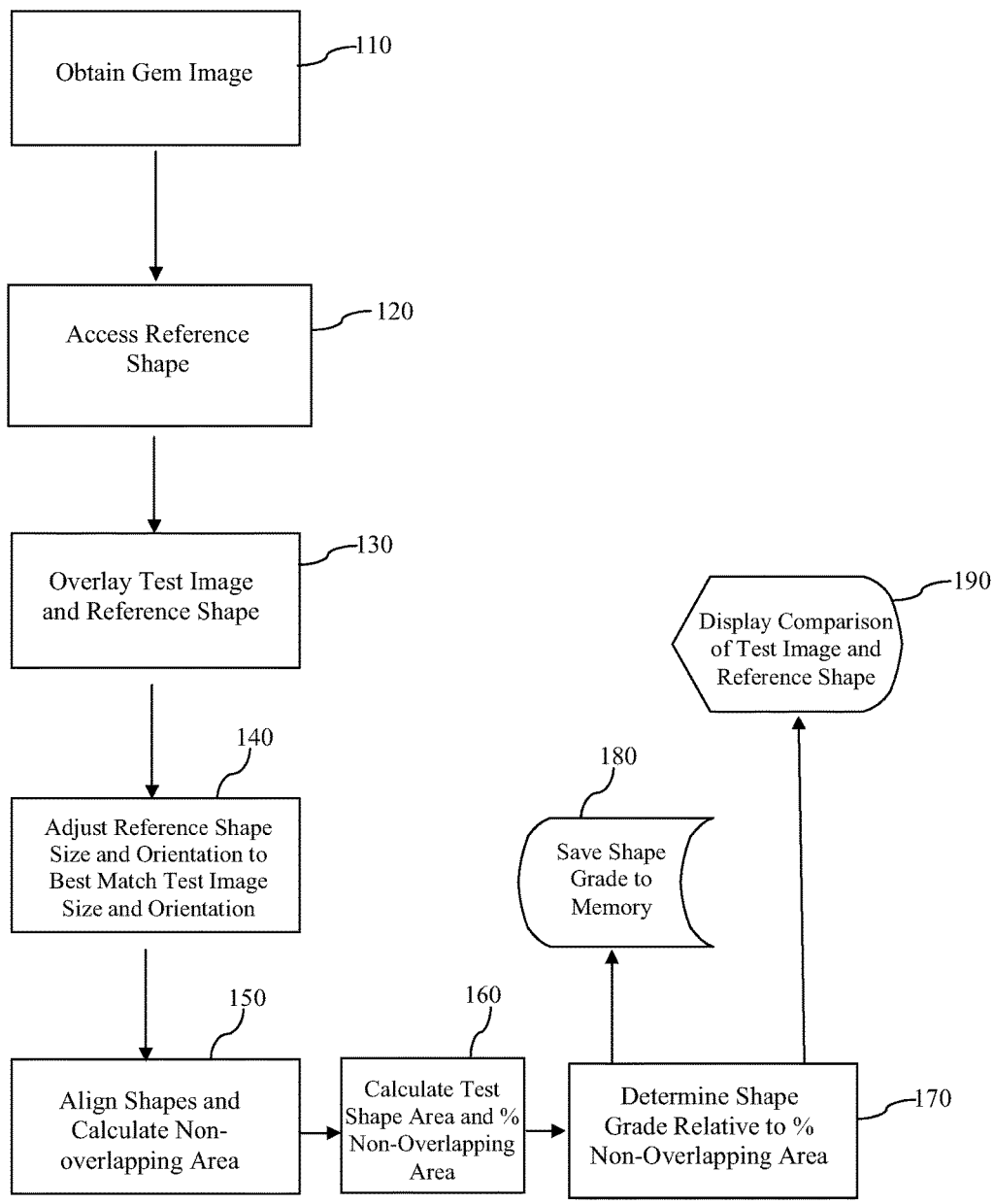
FIG. 2 is a process flow chart, showing an exemplary embodiment of the described method of evaluating gemstone shape.
Figure 3A:
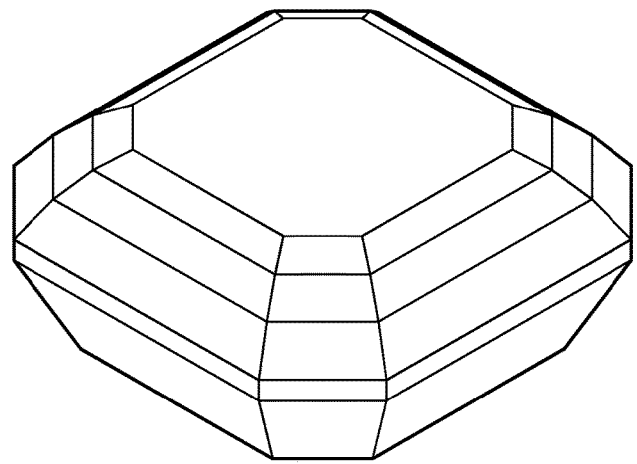
FIG. 3A shows a top perspective view.
Figure 3B:
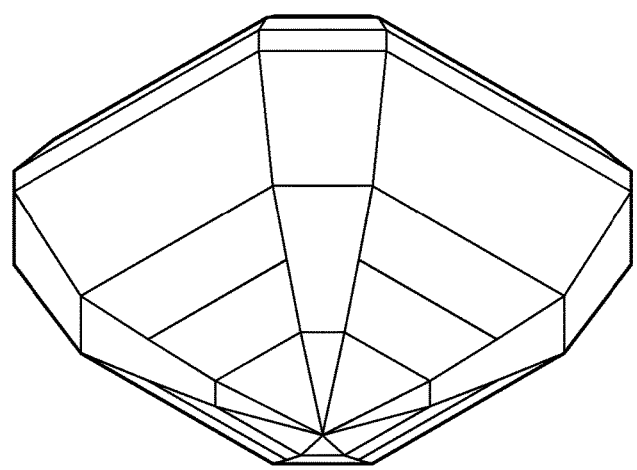
FIG. 3B shows a bottom perspective view.
Figure 3C:
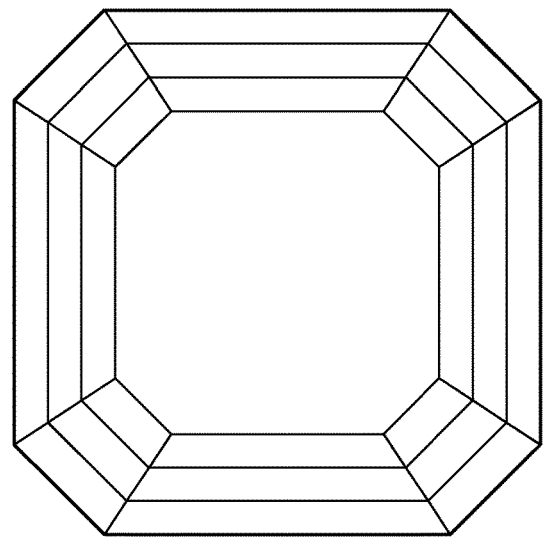
FIG. 3C shows a top (table) view.
Figure 3D:
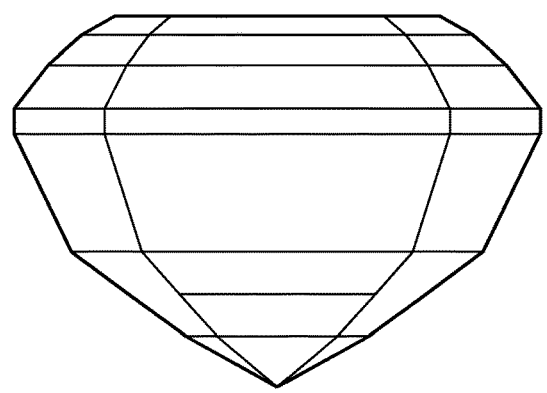
FIG. 3D shows a first side view.
Figure 3E:
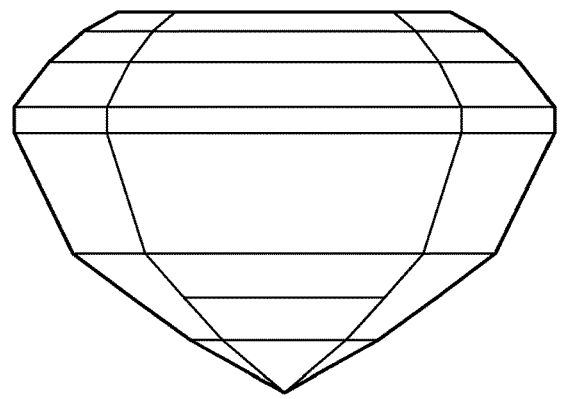
FIG. 3E shows a second side view.
Figure 3F:
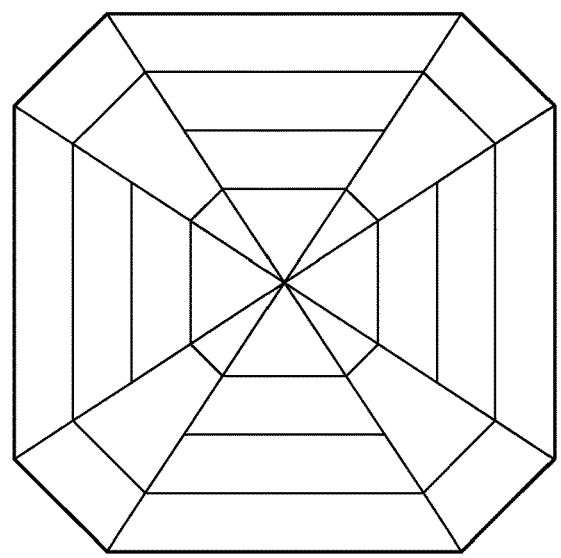
FIG. 3F shows a bottom (culet) view.
Figure 3G:
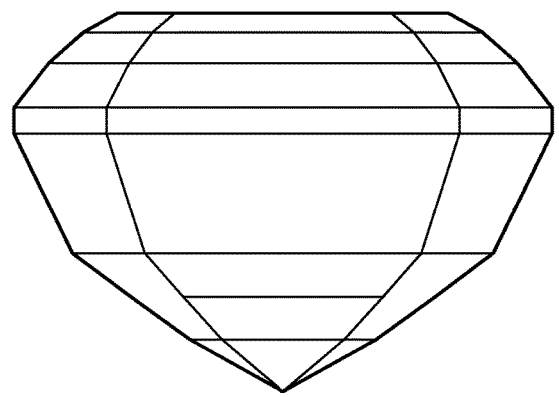
FIG. 3G shows a third side view.
Figure 3H:
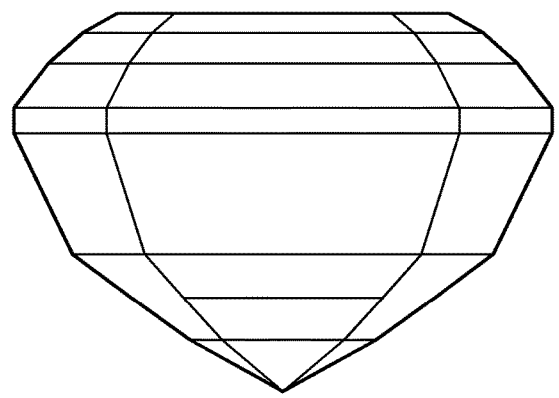
FIG. 3H shows a fourth side view.
Figure 4A:
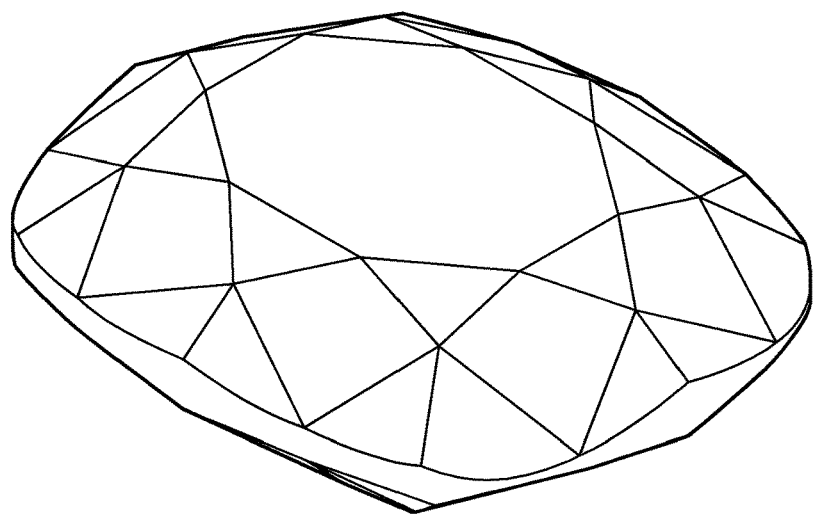
FIG. 4A shows a top perspective view.
Figure 4B:
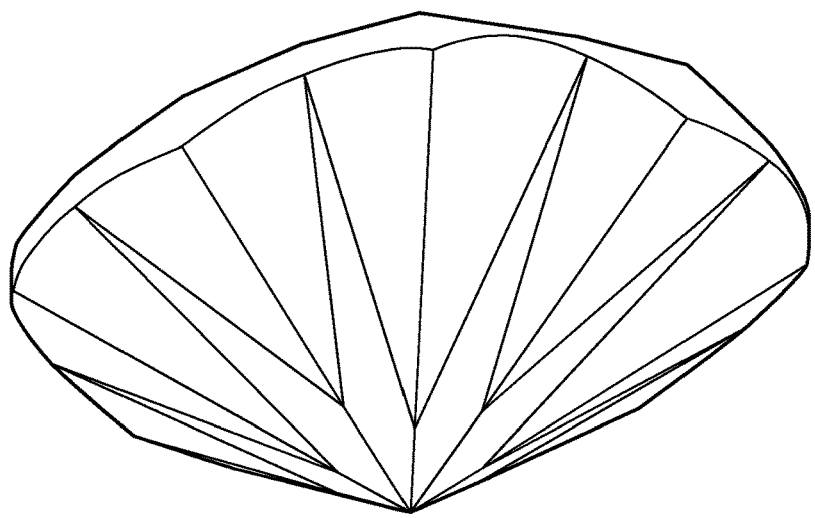
FIG. 4B shows a bottom perspective view.
Figure 4C:
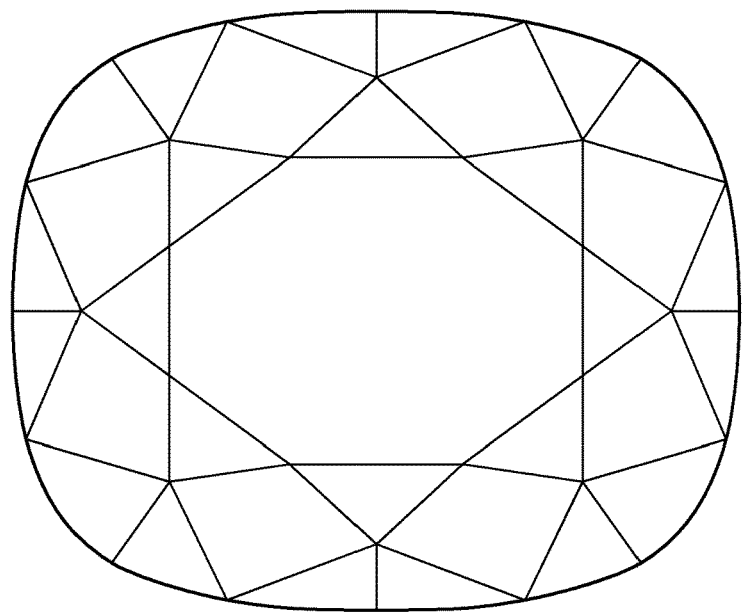
FIG. 4C shows a top (table) view.
Figure 4D:
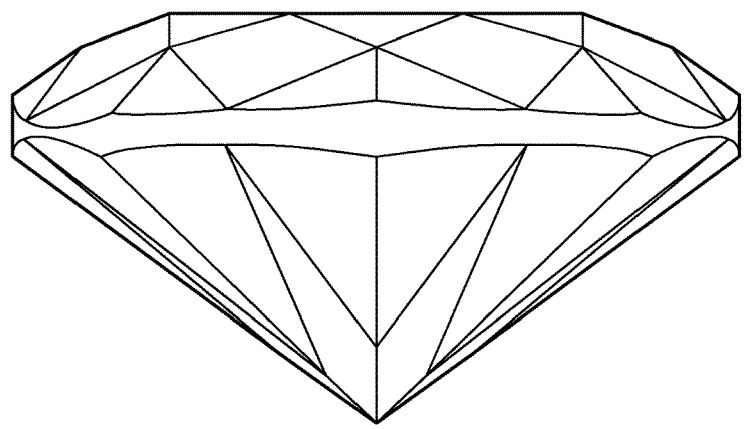
FIG. 4D shows a first side view.
Figure 4E:
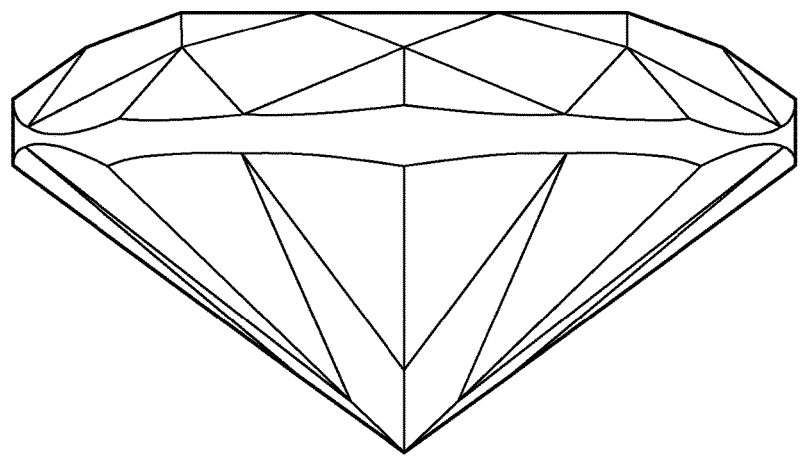
FIG. 4E shows a second side view.
Figure 4F:
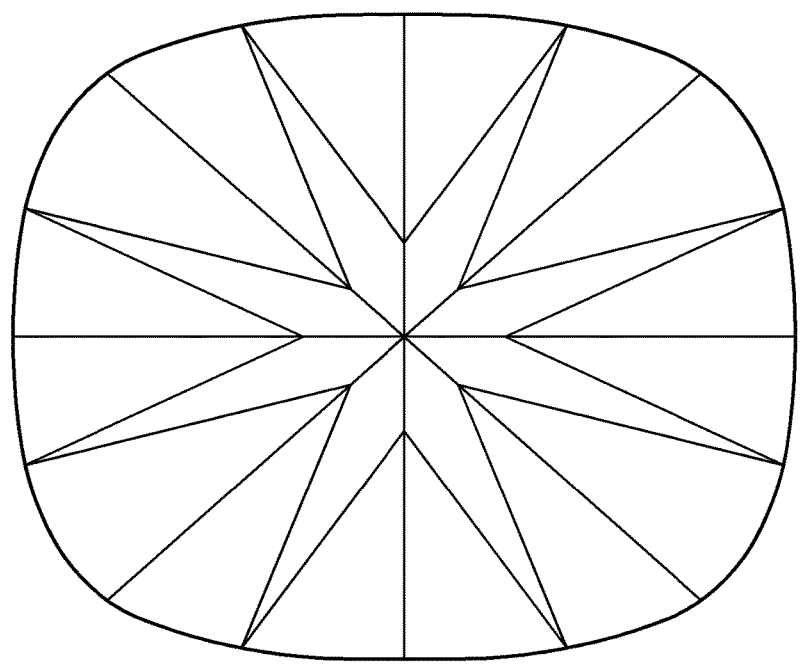
FIG. 4F shows a bottom (culet) view.
Figure 4G:
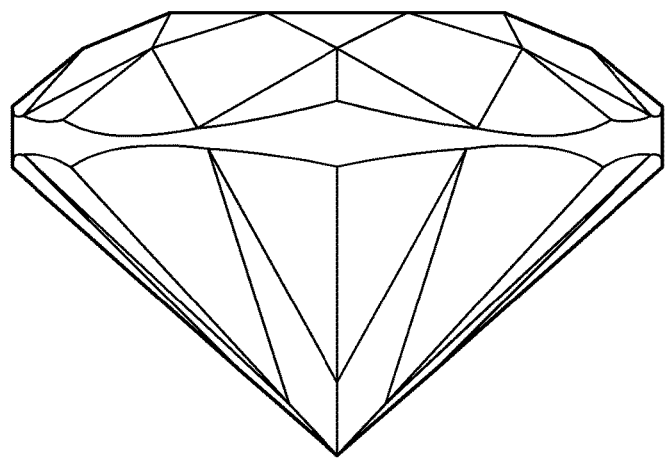
FIG. 4G shows a third side view.
Figure 4H:
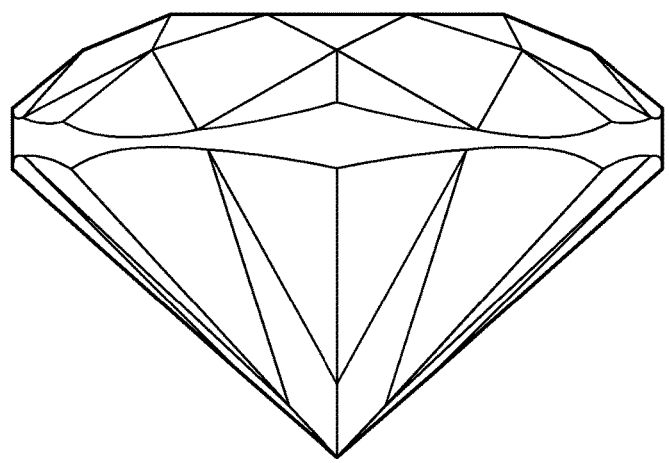
FIG. 4H shows a fourth side view.
Figure 5A:
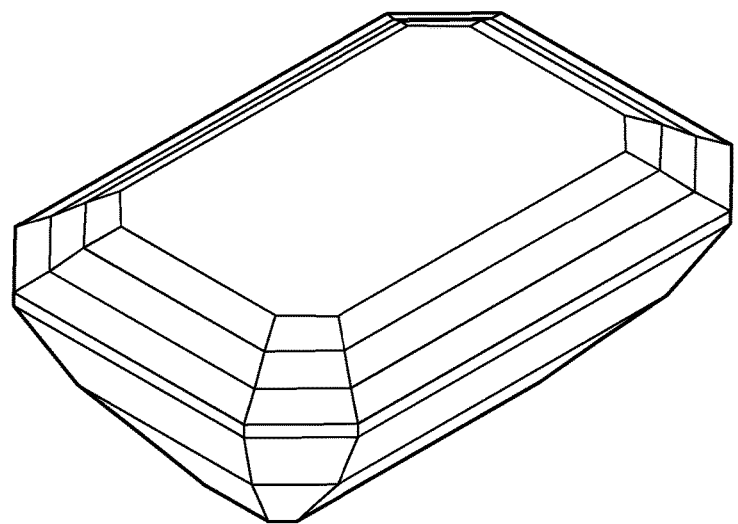
FIG. 5A shows a top perspective view.
Figure 5B:
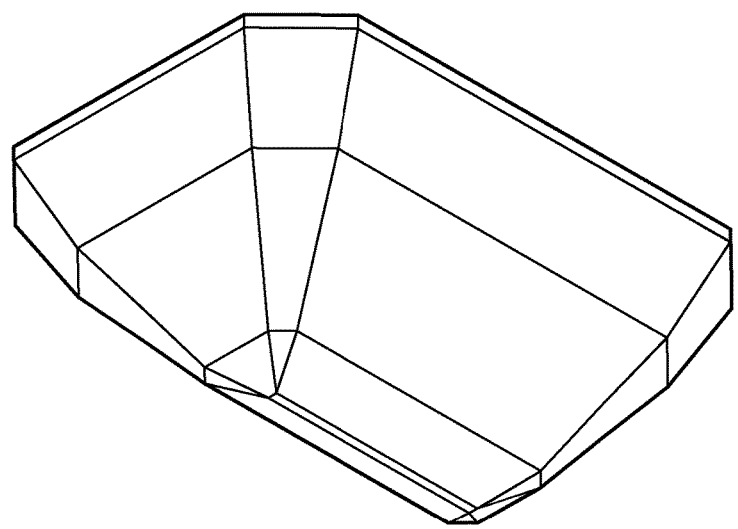
FIG. 5B shows a bottom perspective view.
Figure 5C:
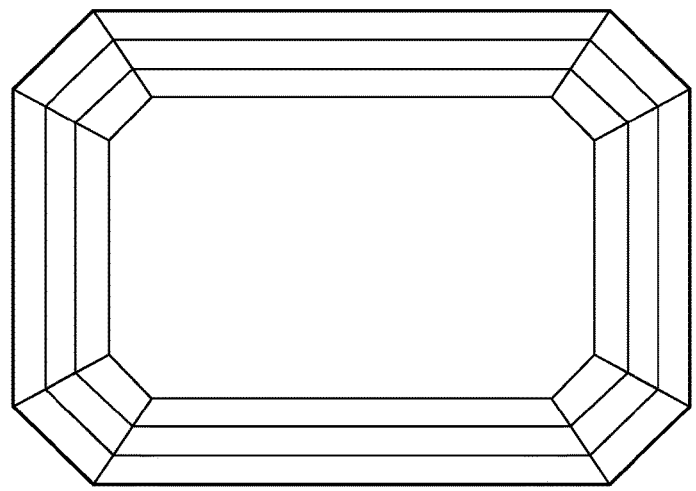
FIG. 5C shows a top (table) view.
Figure 5D:
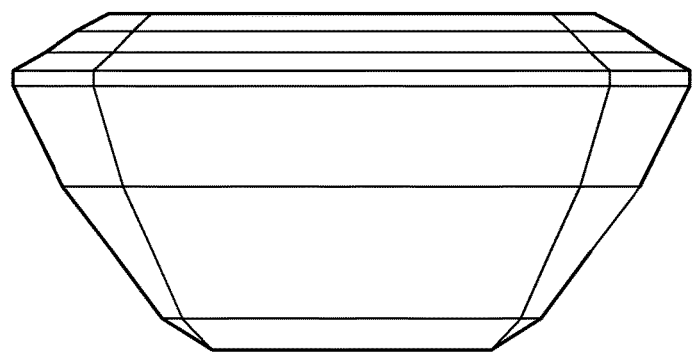
FIG. 5D shows a first side view.
Figure 5E:
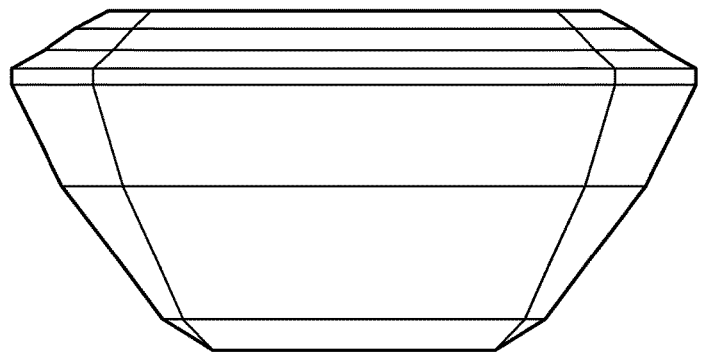
FIG. 5E shows a second side view.
Figure 5F:
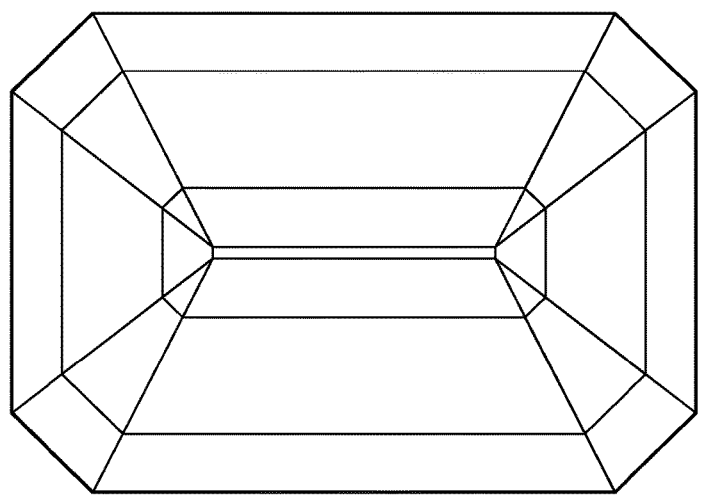
FIG. 5F shows a bottom (culet) view.
Figure 5G:
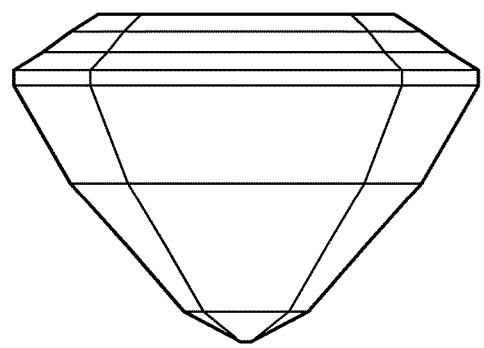
FIG. 5G shows a third side view.
Figure 5H:
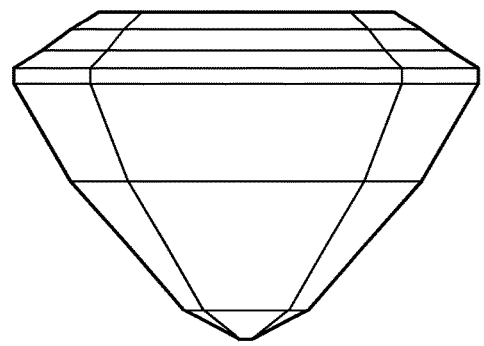
FIG. 5H shows a fourth side view.
Figure 6A:
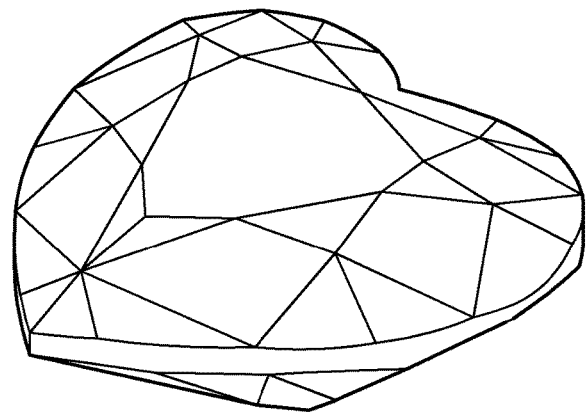
FIG. 6A shows a top perspective view.
Figure 6B:
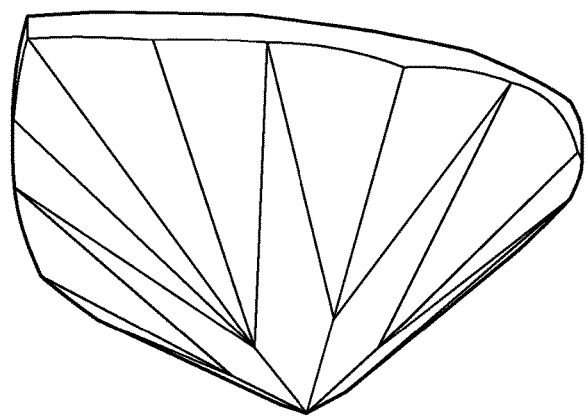
FIG. 6B shows a bottom perspective view.
Figure 6C:
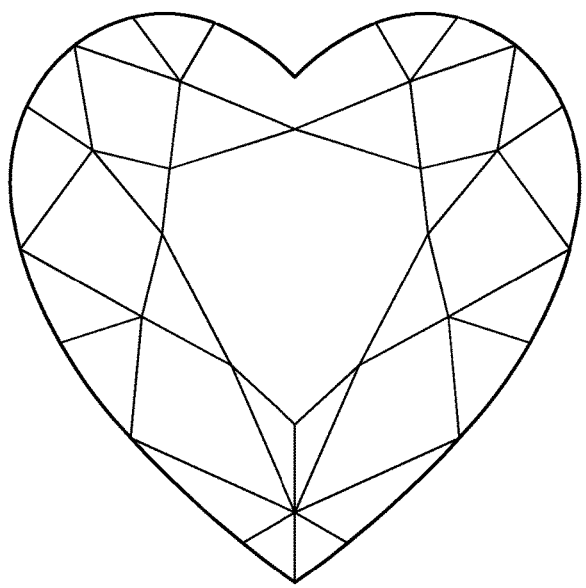
FIG. 6C shows a top (table) view.
Figure 6D:
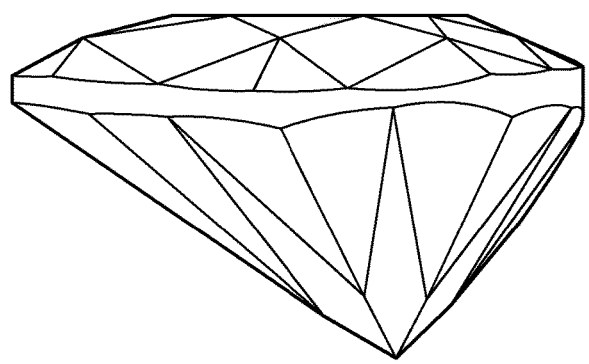
FIG. 6D shows a first side view.
Figure 6E:
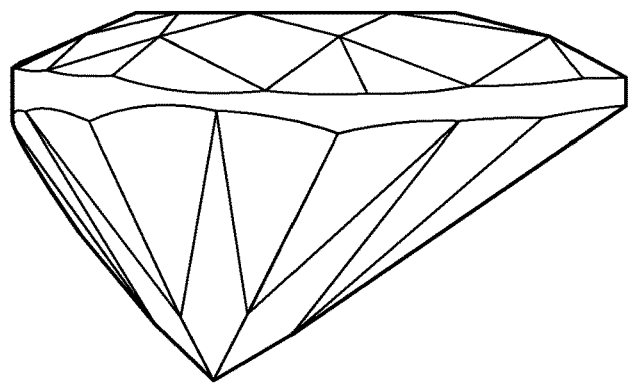
FIG. 6E shows a second side view.
Figure 6F:
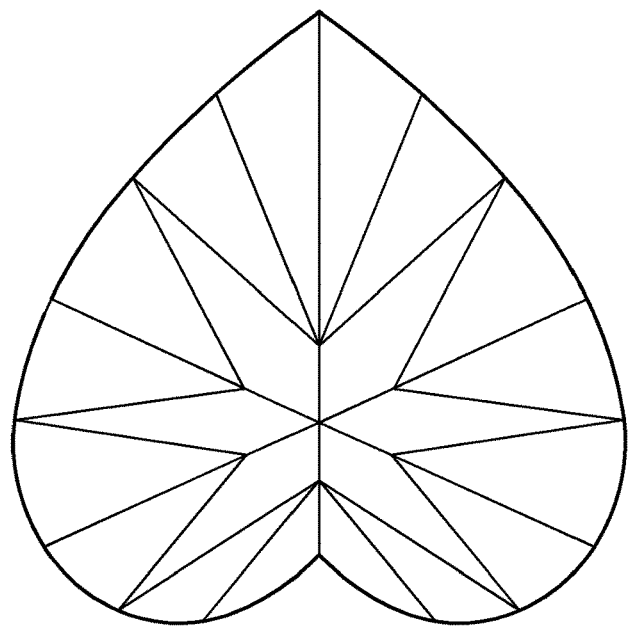
FIG. 6F shows a bottom (culet) view.
Figure 6G:
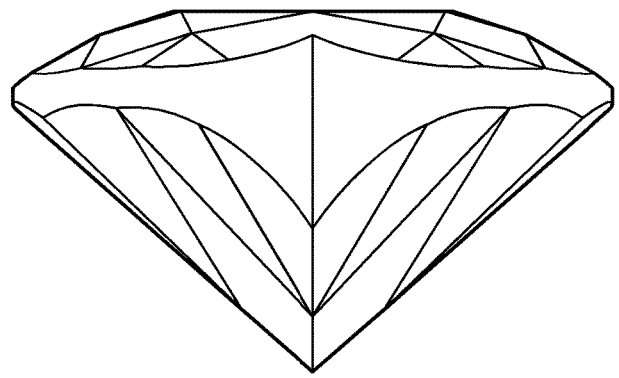
FIG. 6G shows a third side view.
Figure 6H:
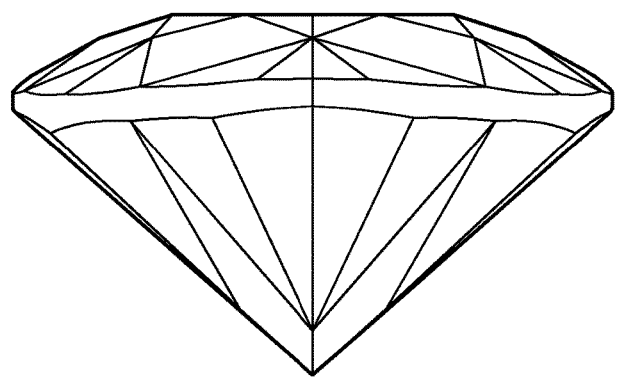
FIG. 6H shows a fourth side view.
Figure 7A:
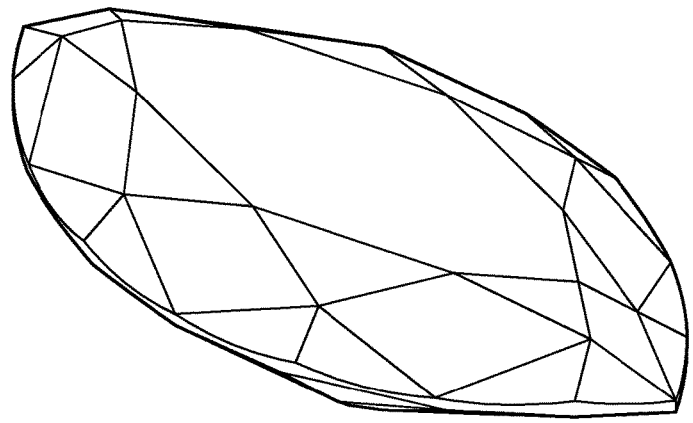
FIG. 7A shows a top perspective view.
Figure 7B:
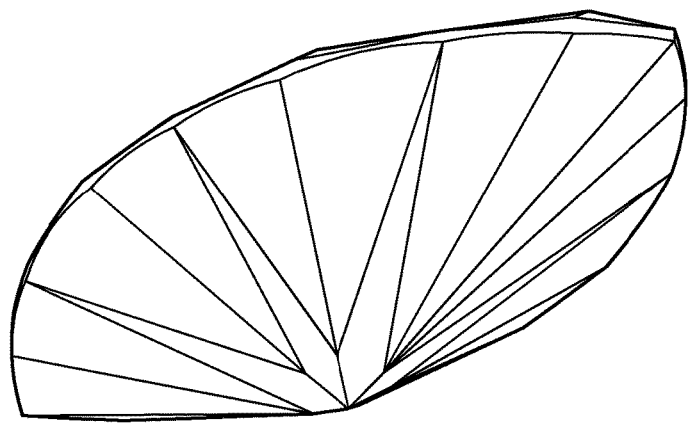
FIG. 7B shows a bottom perspective view.
Figure 7C:
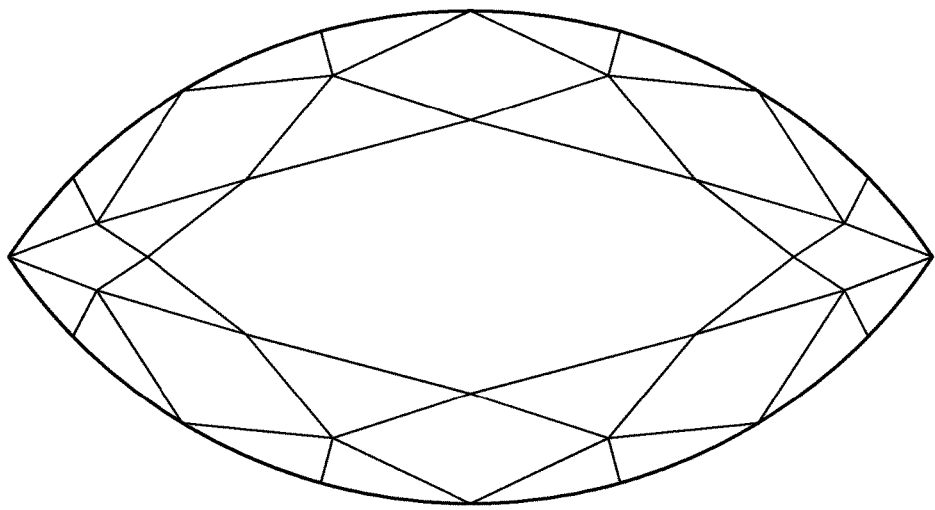
FIG. 7C shows a top (table) view.
Figure 7D:
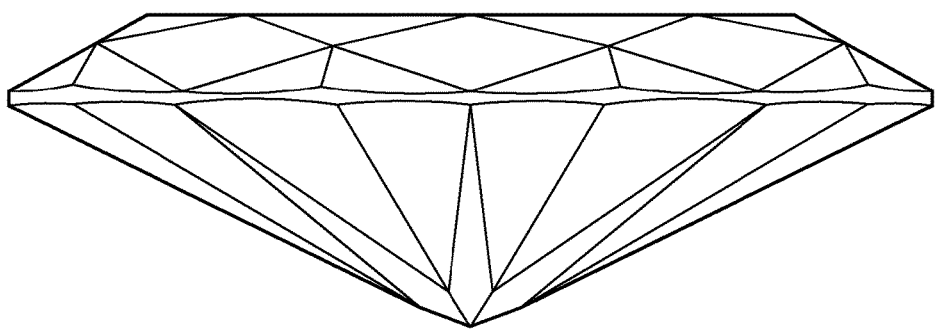
FIG. 7D shows a first side view.
Figure 7E:
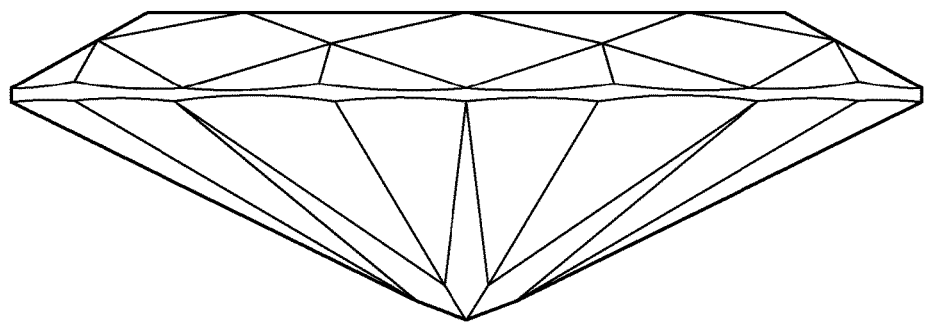
FIG. 7E shows a second side view.
Figure 7F:
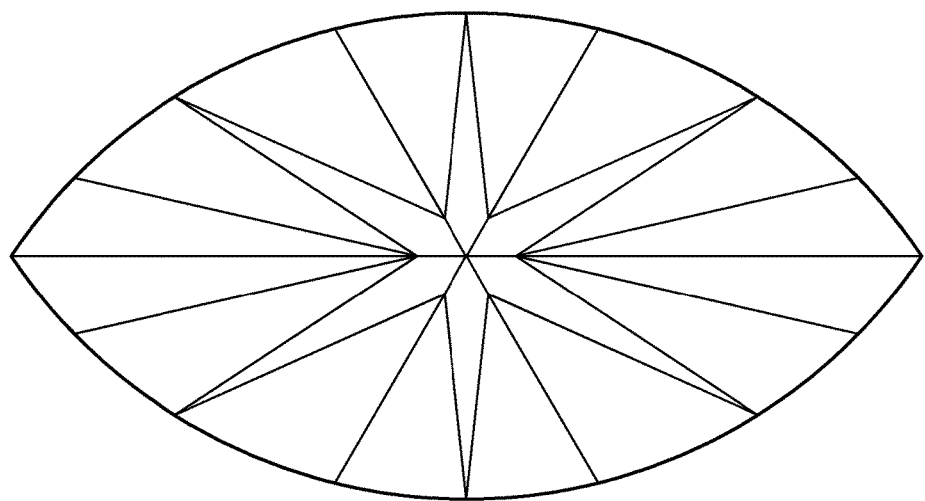
FIG. 7F shows a bottom (culet) view.
Figure 7G:
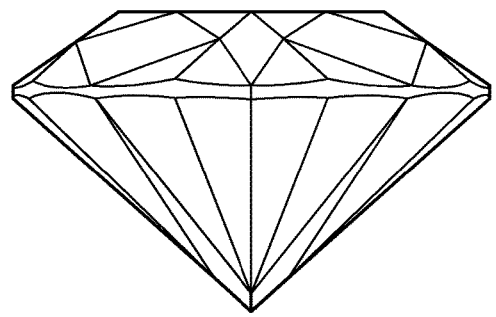
FIG. 7G shows a third side view.
Figure 7H:
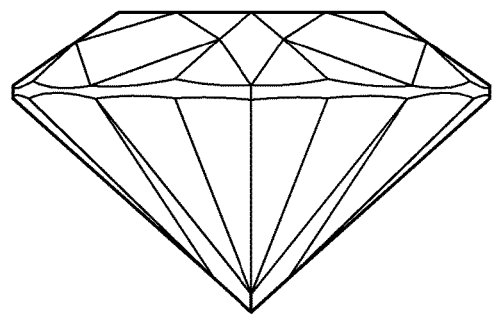
FIG. 7H shows a fourth side view.
Figure 8A:
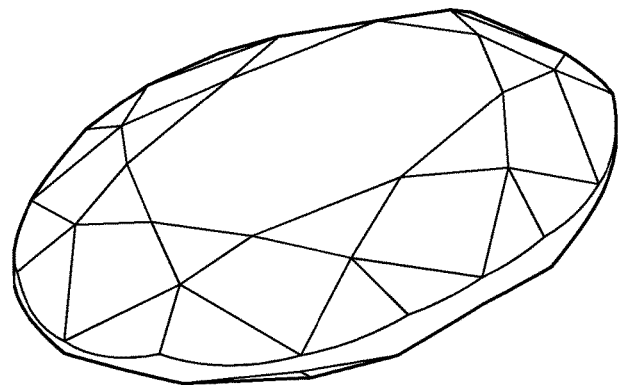
FIG. 8A shows a top perspective view.
Figure 8B:
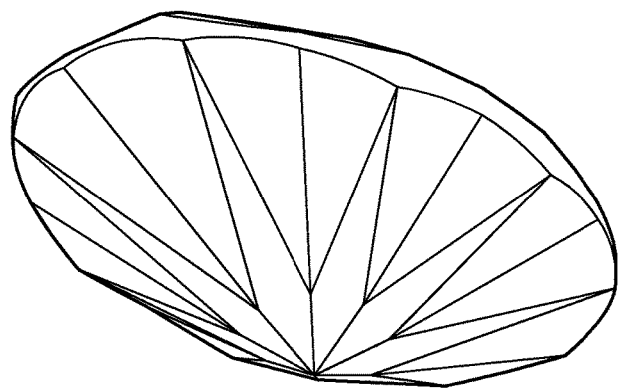
FIG. 8B shows a bottom perspective view.
Figure 8C:
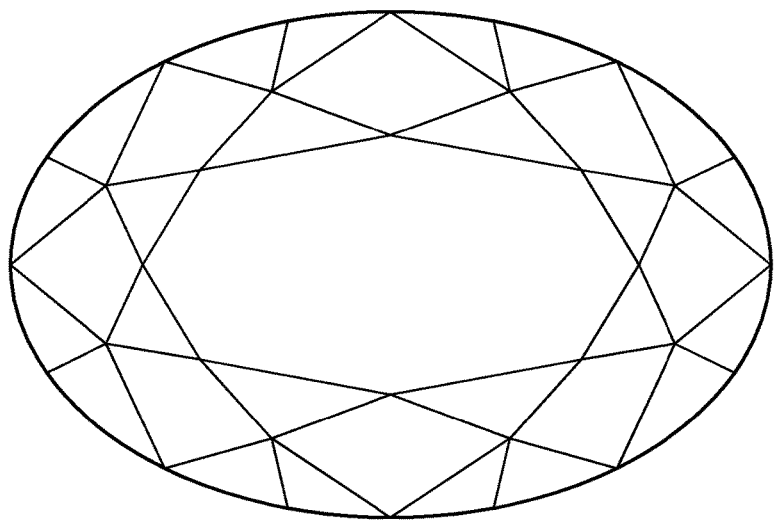
FIG. 8C shows a top (table) view.
Figure 8D:
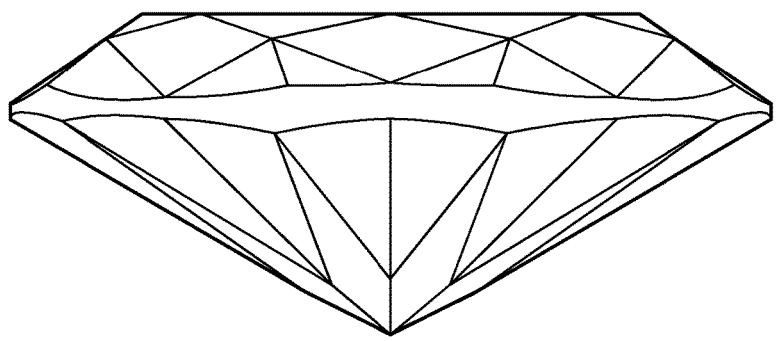
FIG. 8D shows a first side view.
Figure 8E:
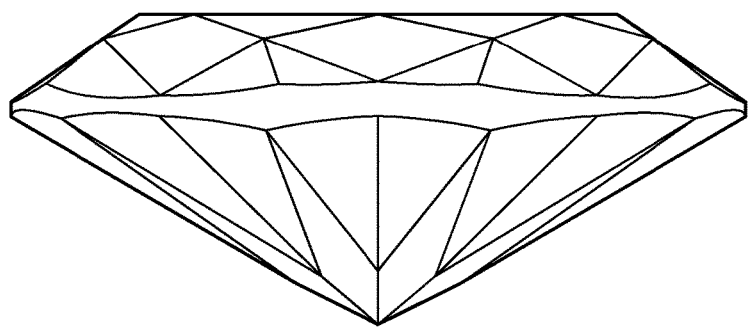
FIG. 8E shows a second side view.
Figure 8F:
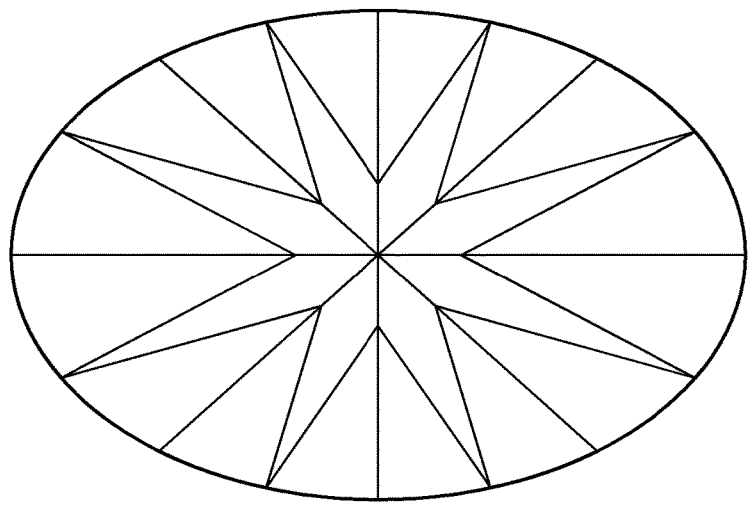
FIG. 8F shows a bottom (culet) view.
Figure 8G:
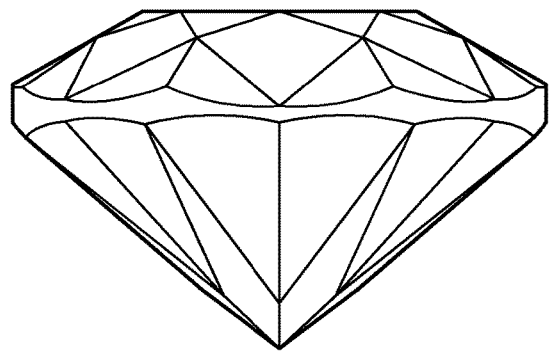
FIG. 8G shows a third side view.
Figure 8H:
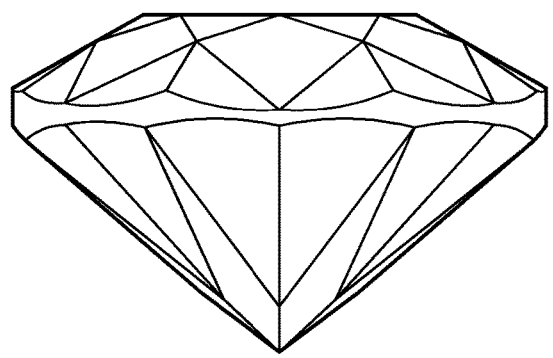
FIG. 8H shows a fourth side view.
Figure 9A:
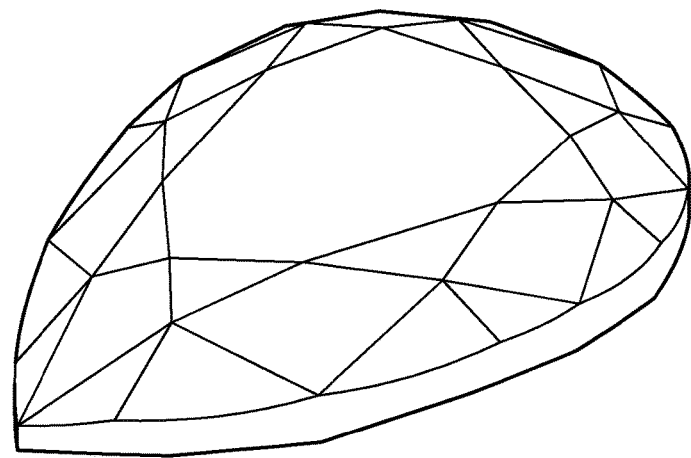
FIG. 9A shows a top perspective view.
Figure 9B:
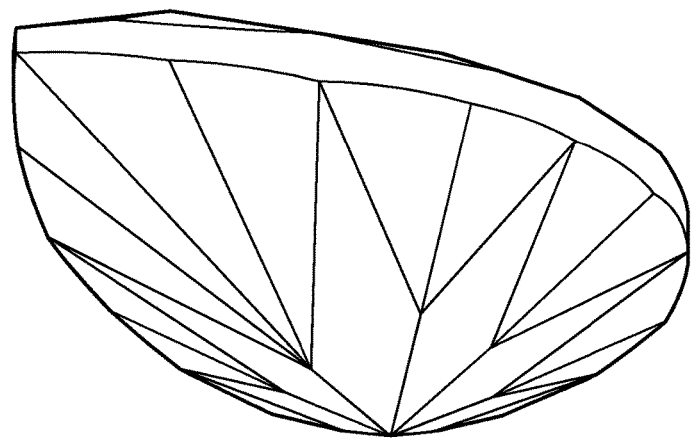
FIG. 9B shows a bottom perspective view.
Figure 9C:
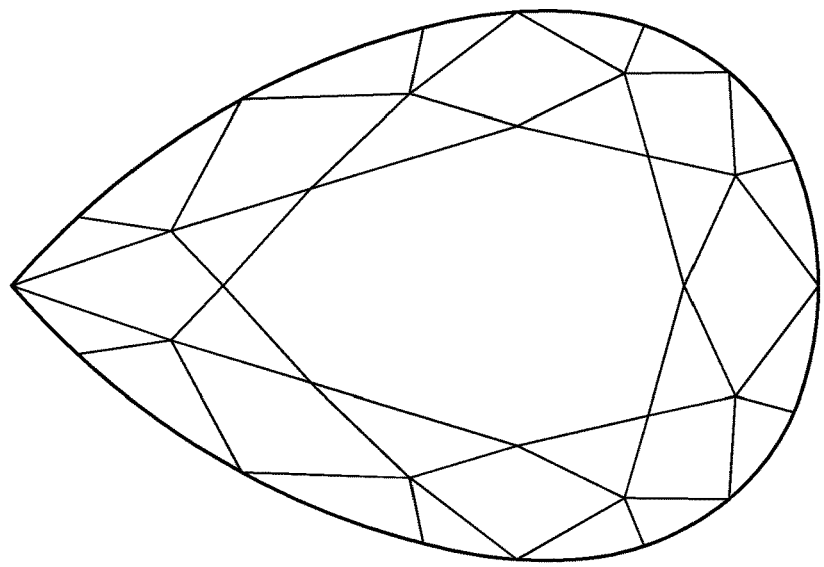
FIG. 9C shows a top (table) view.
Figure 9D:
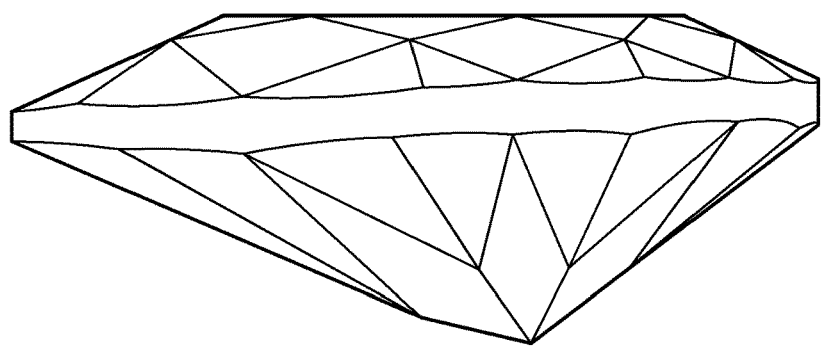
FIG. 9D shows a first side view.
Figure 9E:
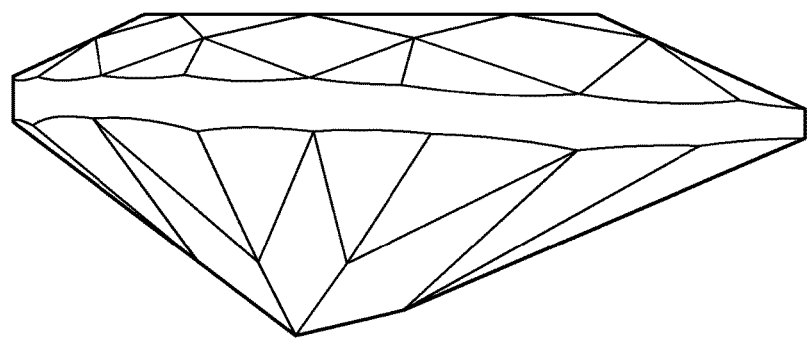
FIG. 9E shows a second side view.
Figure 9F:
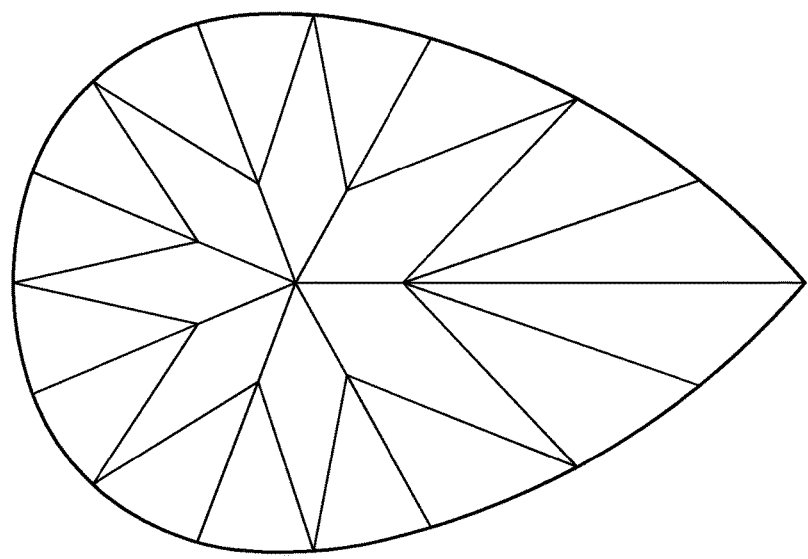
FIG. 9F shows a bottom (culet) view.
Figure 9G:
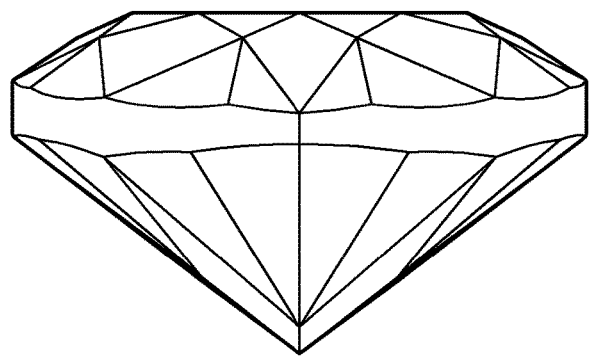
FIG. 9G shows a third side view.
Figure 9H:
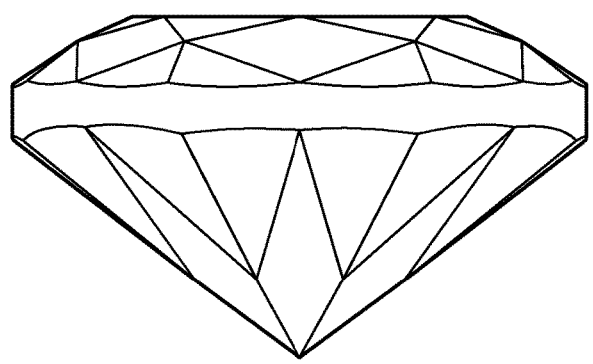
FIG. 9H shows a fourth side view.
Figure 10A:
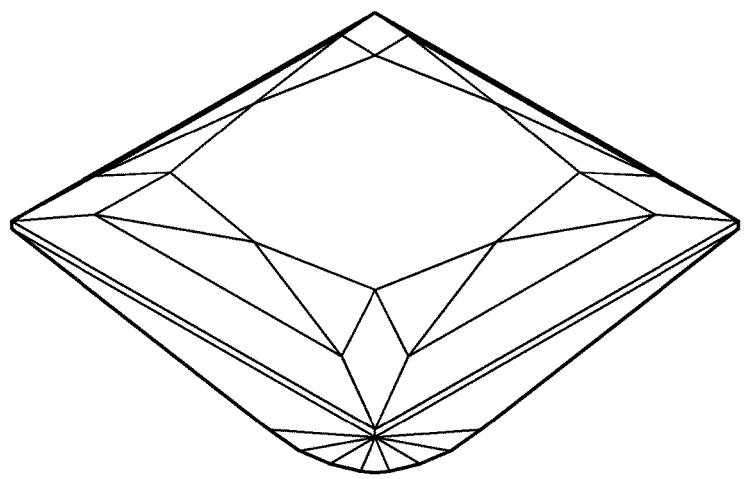
FIG. 10A shows a top perspective view.
Figure 10B:
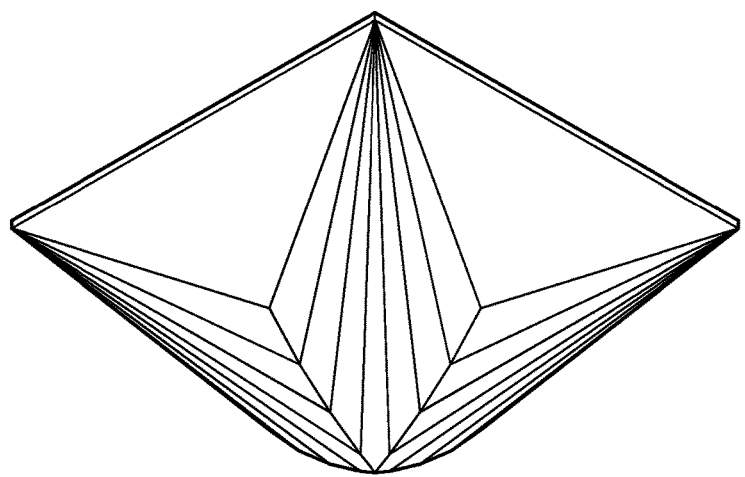
FIG. 10B shows a bottom perspective view.
Figure 10C:
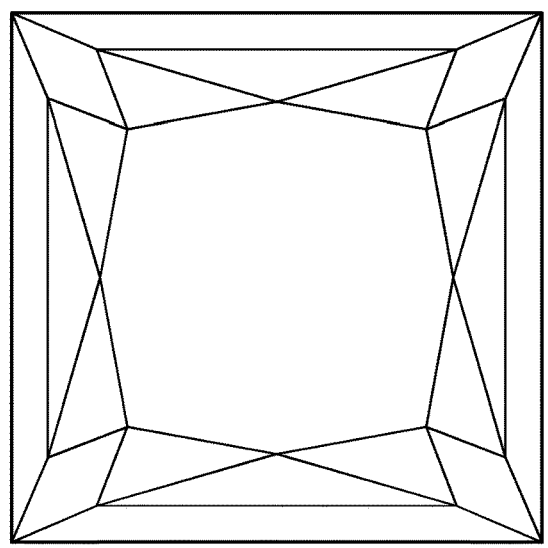
FIG. 10C shows a top (table) view.
Figure 10D:
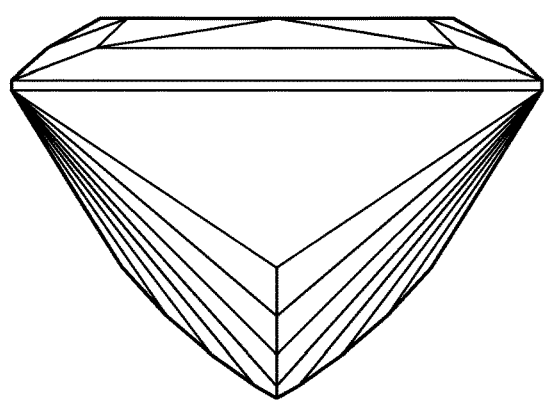
FIG. 10D shows a first side view.
Figure 10E:
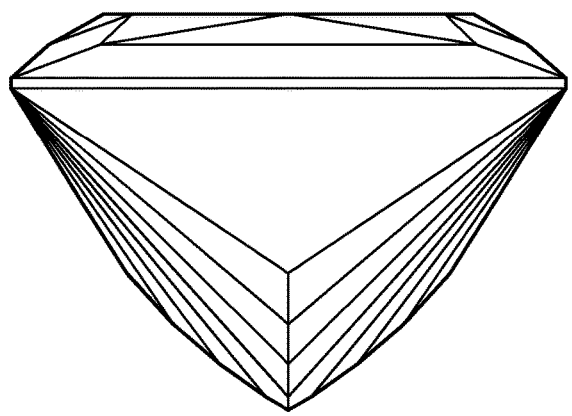
FIG. 10E shows a second side view.
Figure 10F:
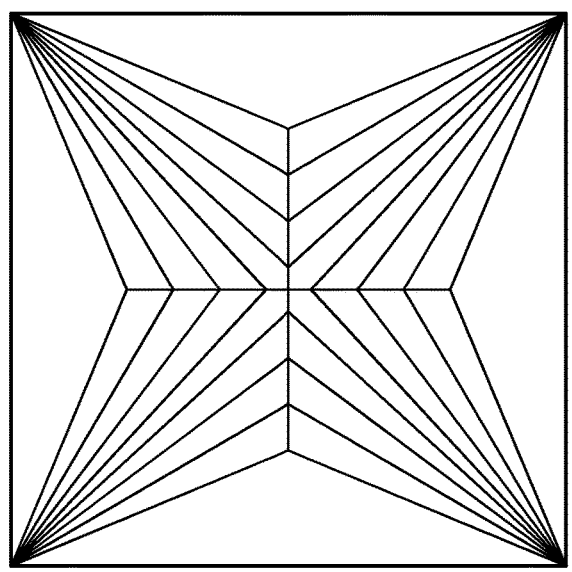
FIG. 10F shows a bottom (culet) view.
Figure 10G:
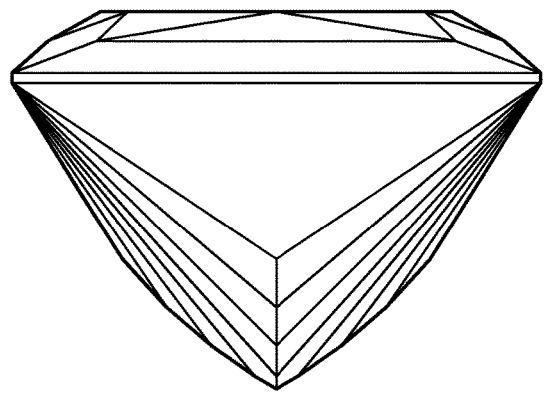
FIG. 10G shows a third side view.
Figure 10H:
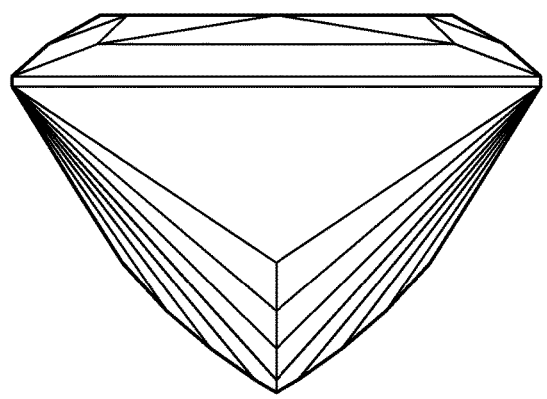
FIG. 10H shows a fourth side view.
Figure 11A:
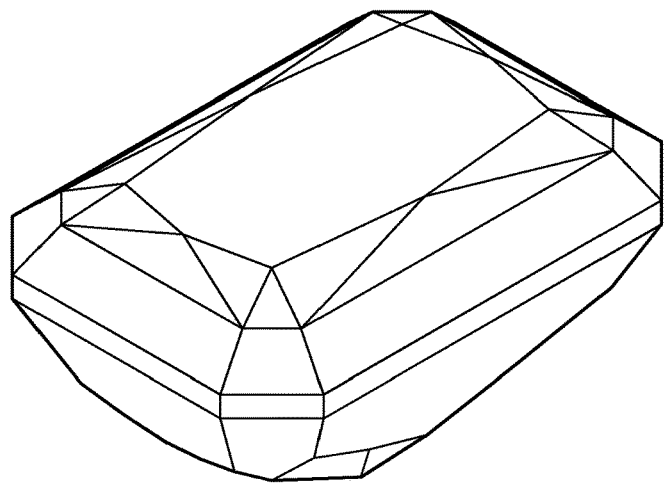
FIG. 11A shows a top perspective view.
Figure 11B:
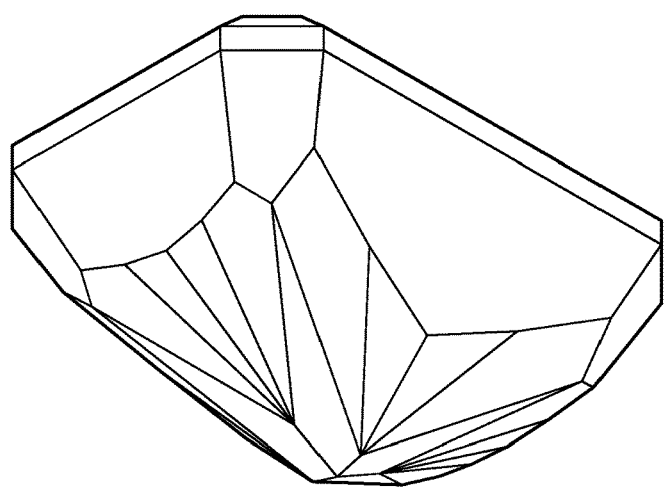
FIG. 11B shows a bottom perspective view.
Figure 11C:
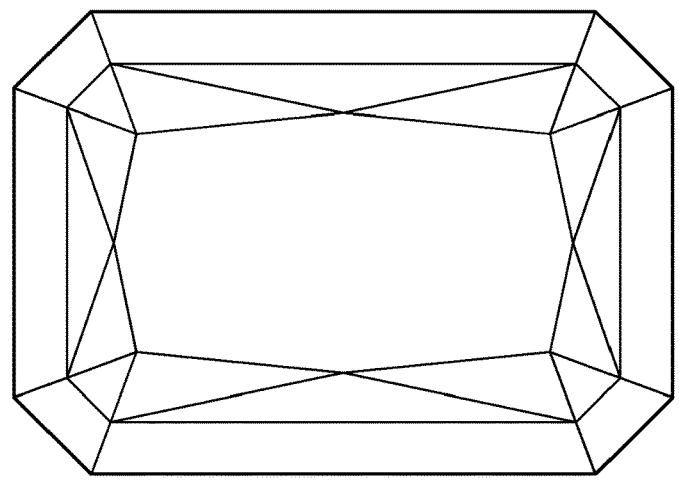
FIG. 11C shows a top (table) view.
Figure 11D:
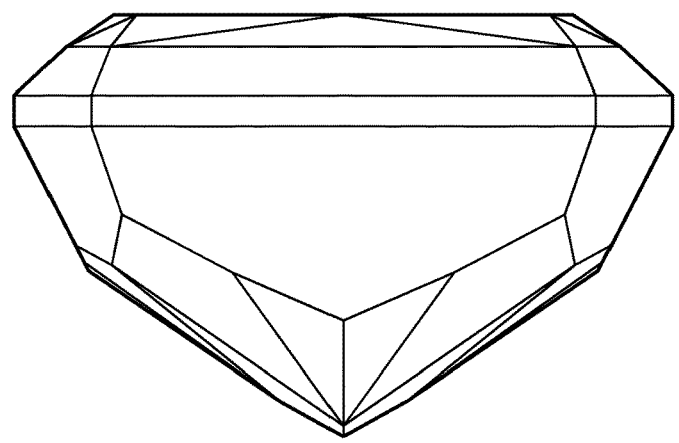
FIG. 11D shows a first side view.
Figure 11E:
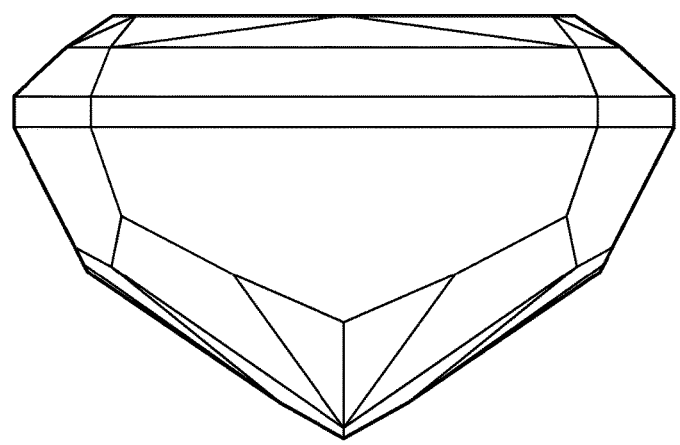
FIG. 11E shows a second side view.
Figure 11F:
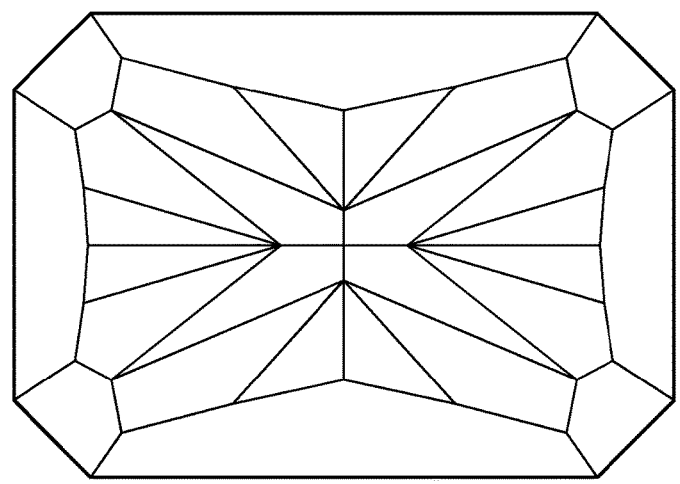
FIG. 11F shows a bottom (culet) view.
Figure 11G:
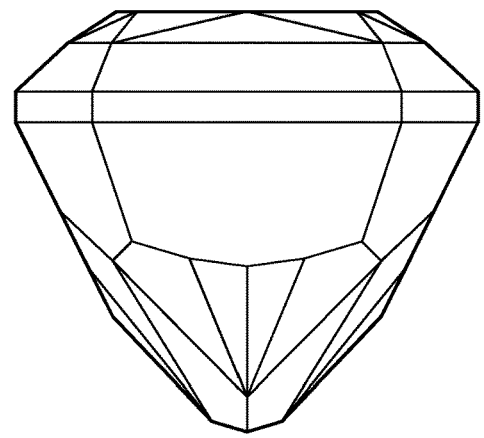
FIG. 11G shows a third side view.
Figure 11H:
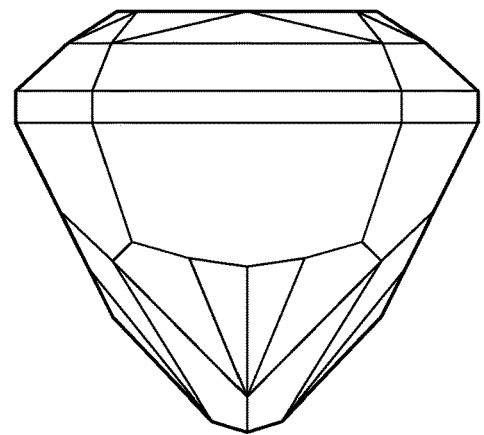
FIG. 11H shows a fourth side view.
Figure 12A:
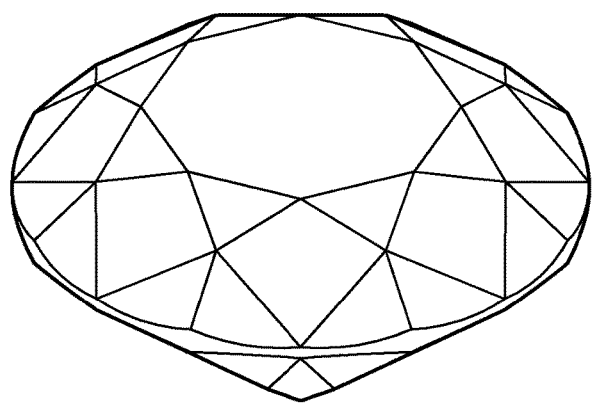
FIG. 12A shows a top perspective view.
Figure 12B:
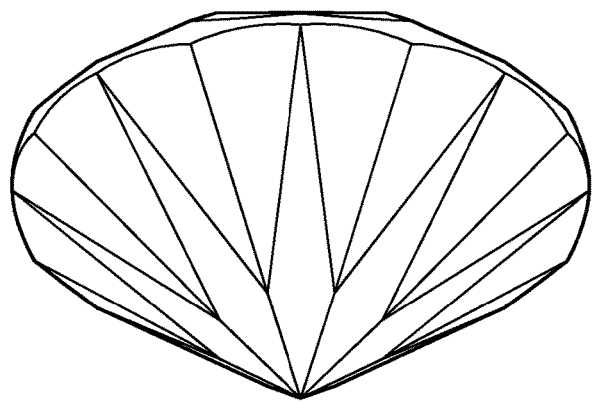
FIG. 12B shows a bottom perspective view.
Figure 12C:
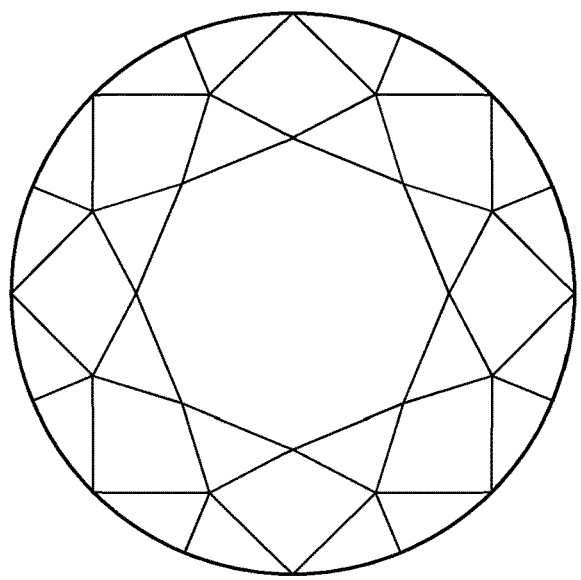
FIG. 12C shows a top (table) view.
Figure 12D:
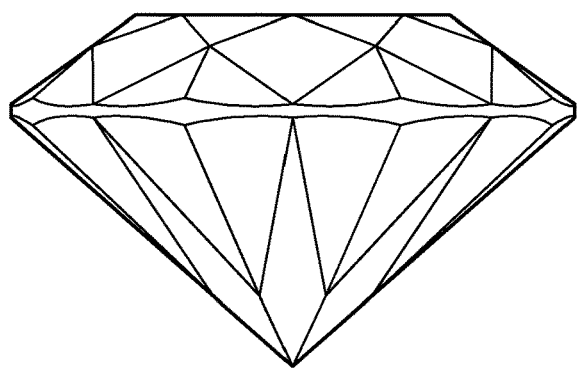
FIG. 12D shows a first side view.
Figure 12E:
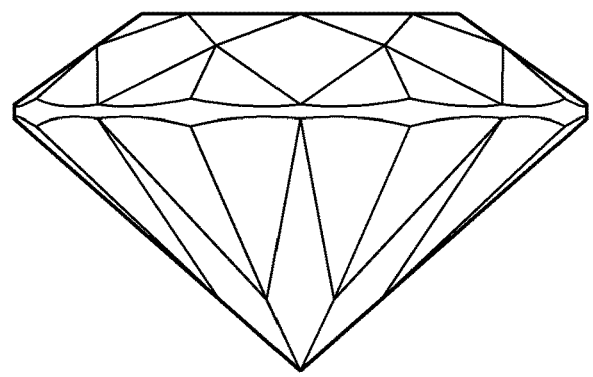
FIG. 12E shows a second side view.
Figure 12F:
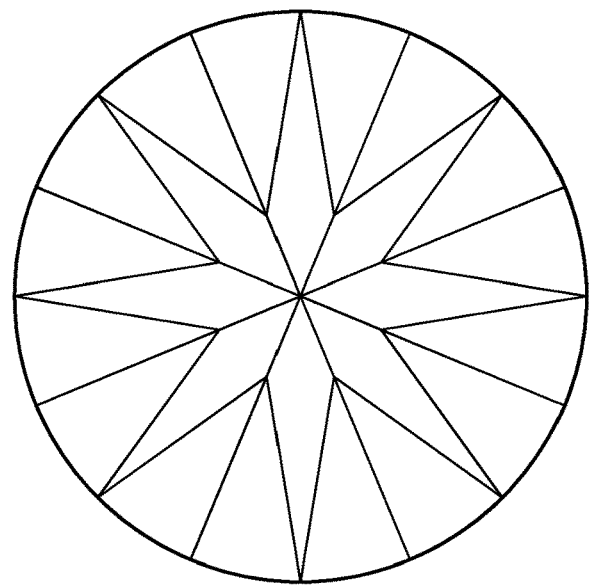
FIG. 12F shows a bottom (culet) view.
Figure 12G:
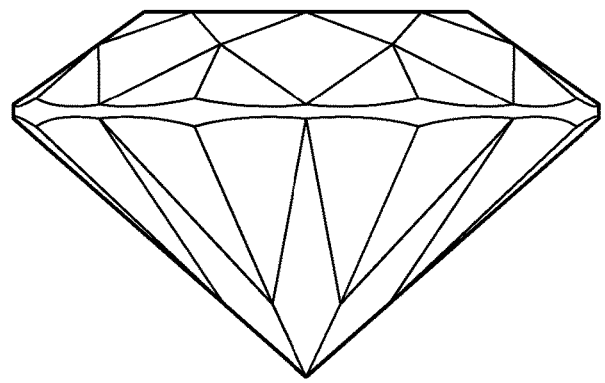
FIG. 12G shows a third side view.
Figure 12H:
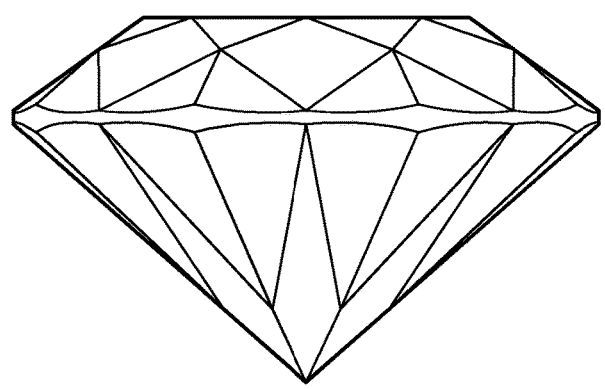
FIG. 12H shows a fourth side view.

An exemplary computer-implemented embodiment of the described methods is shown in FIG. 2. With reference to FIG. 2, the process of evaluating a gem shape begins with obtaining a test gem image (110). The test gem can be any precious or semi-precious gem. Non-limiting examples of precious gems include diamond, ruby, sapphire, and emerald. Non-limiting examples of semi-precious gems include amethyst, apatite, aquamarine, pearl, sphalerite, spessartite garnet, and the like. In a particular example, the test gem is a "cut gem" that has been prepared for the auction, wholesale, or retail markets. In another example, the test is "rough" and is suitable for sale to gem processors.

In particular embodiments, obtaining a test gem image (110) is achieved using the camera (50, FIG. 1) to acquire the image. In particular examples, the camera is a digital camera, including a digital camera using a charged coupled device (CCD) sensor, or a digital camera using a complementary metal oxide semiconductor (CMOS) sensor. The camera can be capable of acquiring still or moving images, but it will be appreciated that cameras capable of acquiring moving images can also acquire still images. As described herein, the camera (50, FIG. 1) can be a dedicated gem imaging or grading system for example, but not limited to, the DIAMENSION® diamond proportion and cut grading system (Sarin Technologies, Ltd., Kfar Saba, Israel); and the Scanox Proportion HD and UNO Scope HD diamond grading systems (OGI Systems, Ltd., Ramat Gan, Israel).

In other particular embodiments, obtaining a test gem image (110) includes examples wherein a previously-acquired test gem image is accessed from the computer memory (20, FIG. 1). It will be appreciated that the previously-acquired image does not need to have been acquired by use of the camera (50, FIG. 1). In particular examples the previously-acquired image is a digitized version of a hard copy image (e.g. paper, film, slide, transparency, and the like) that was previously stored or newly loaded into the memory (20, FIG. 1). In further examples, obtaining a test gem image (110) includes accessing an image from a database of test gem images in the memory (20, FIG. 1), such as those acquired by any method described herein.

Test gem images for use in the described methods can comprise the entire test gem shape, or can show aspects of the test gem shape (e.g. two-dimensional faces, individual facets, series of facets, close-up views of shape aspects such as curvature, points of intersection between facets, and the like). In particular embodiments, at least one side-view, top-view, or bottom view of the test gem is obtained. In other embodiments, at least one angled perspective of a side-view, top-view, or bottom view of the test gem is obtained. In some examples the obtained image is two-dimensional. In other examples, the obtained image is three-dimensional. In still other examples, multiple still images are obtained, and the processor (10, FIG. 1) aligns and assembles the separate two-dimensional images into a single image.

Once a test gem image (containing the test gem shape) is obtained (110), an image containing a reference representation of the test gem shape (or aspects thereof) is accessed from the computer memory (120). The accessed reference shape is of the same view as the test gem shape (e.g. side, top, bottom, angled and the like).

Gems can be cut into a wide variety of shapes. In a particular embodiment, the image or images of the reference gem shape and multiple variations thereof, include various views (e.g. side, top, bottom, angled and the like) and shape aspects (e.g. one or more two-dimensional faces, curves, or facets). In particular embodiments, the reference shape is a "regular" shape, or any variation thereof. As used herein, a "regular" shape includes, but is not limited to, a circle, oval, square, triangle, diamond, rectangle, and trapezoid. In such embodiments, the reference shape possesses a geometric ideal conformation of a given shape as commonly known in the art (see for example, Jurgensen et al., "McDougal Littell Jurgensen Geometry: Student Edition Geometry 2000," Houghton Mifflin Co., 2000, the contents of which are incorporated by reference). For example, a reference circular gem shape is perfectly circular, with all radii equal to the same value. Similarly, a perfect square gem shape will have four sides of equal length, with each corner possessing a 90 degree angle.

In other embodiments, a test gem is not cut into a "regular" geometric shape, but is comparable to one or more "regular" geometric shapes. For example, the top view of some variations of a "Round" cut diamond can be compared with an ideal circle, whereas the side view of the same particular "Round" diamond can be compared with a triangle. Similarly, the top-view of an "Emerald" cut diamond can be compared with a rectangle.

The test gem shape and the at least one reference shape for use in the described methods can be any ideal version of a "fancy" gem shape know in the art, or any variation thereof. In particular embodiments, the reference shape or shapes comprise the ideal shape, but one or more aspects have been varied according to particular styles and the like. For example, the test shape can comprise a "pear" shape; and the reference shapes are one or more "pear" shapes, which may vary in particular aspects from an ideal pear shape.

In other embodiments, the test gem shape (in the test gem image) is compared with one or more views or one or more variations of a reference cut gem shape such as, but not limited to, Heart, Emerald, Radiant, Rectangle, Princess, Marquise, S. French Marquise, Oval, Cushion, Pear, Pearmirage, French Pearmirage, French Pear, French Marquiz, Round, Asscher, and Trilliant, or any variation thereof. In other particular embodiments, the test gem is compared with one or more views of a reference rough gem shape such as, but not limited to, Octahedron, Sawable, Cleavage, Makable, Flat, Crystal, and Maacle, or any variation thereof.

Images containing reference shapes (a "reference shape image") can be prepared by any method known in the art. In particular embodiments, a reference shape is rendered using computer assisted design software. In other embodiments, a reference shape is hand-drawn and scanned into a computer for later use. In still other embodiments, the reference shape is based on a cut gemstone which has been scanned and graded by a gemstone grading machine. In still further embodiments, a reference shape is based on a hard copy image (e.g. paper or otherwise) that is scanned into a computer.

Particular examples of reference shapes for use in evaluating a test shape are disclosed herein in FIGS. 3-12, though it will be understood that the methods described herein are not limited to the exact dimensions of the reference shapes illustrated in the figures.

In addition, illustrative relative dimensions of several reference shapes are presented below in Tables 1-14. Ranges of the presented % dimensions and angles are shown. In the following tables, "Table Size" is the top table facet length, divided by the full girdle length; "Total Depth" is the full height of the gem divided by the length of the girdle.

TABLE 1

Relative Reference Heart Dimensions (top view)

| Parameter | From. | To. |
| --- | --- | --- |
| Girdle Thickness (M) | 2.4 | 4 |
| Table size | 57 | 63 |
| Crown Angle | 32 | 36 |
| Pavilion Angle | 38 | 42 |
| Total Depth | 58 | 63 |
| Natural Culet | | 0 |
| Natural Diameter | | 0 |
| Culet Off-Center Width | 0 | 0 |
| Culet Off-Center Length | 0 | 0 |
| Table Off-Center Width | 0 | 0 |
| Table Off-Center Length | 0 | 0 |
| L\W Ratio | 0.87 | 1 |
| Girdle Bending | 50 | 50 |
| Culet Size | 0 | 0 |

TABLE 2

Relative Reference Emerald Dimensions (top view)

| Parameter | From | To |
| --- | --- | --- |
| Girdle Thickness (M) | 2 | 4.5 |
| Table size | 55 | 63 |
| Total Depth | 62 | 72 |
| Natural Cult | | 0 |
| Natural Diameter | | 0 |
| Culet Off-Center Width | 0 | 0 |
| Culet Off-Center Length | 0 | 0 |
| Table Off-Center Width | 0 | 0 |
| Table Off-Center Length | 0 | 0 |
| L\W Ratio | 1.4 | 1.6 |
| Efficiency | 140 | 160 |
| Culet Size | 0 | 0 |
| Pavilion Angle 1 | 48 | 55 |
| Pavilion Angle 2 | 41 | 43 |
| Pavilion Angle 3 | 28 | 32 |
| Pavilion Depth 1 | 43 | 47 |
| Pavilion Depth 2 | 75 | 80 |
| Crown Angle 1 | 45 | 50 |
| Crown Angle 2 | 40 | 44 |

TABLE 2-continued

Relative Reference Emerald Dimensions (top view)

| Parameter | From | To |
|---|---|---|
| Crown Angle 3 | 28 | 35 |
| Crown Height 1 | 45 | 48 |
| Crown Height 2 | 73 | 77 |

TABLE 3

Relative Reference Radiant Dimensions (top view)

| Parameter | From | To |
|---|---|---|
| Girdle Thickness (M) | 2.4 | 4 |
| Table size | 62 | 73 |
| Crown Angle | 38 | 41 |
| Pavilion Angle | 34 | 40 |
| Total Depth | 62 | 73 |
| Culet Off-Center Width | 0 | 0 |
| Culet Off-Center Length | 0 | 0 |
| Table Off-Center Width | 0 | 0 |
| Table Off-Center Length | 0 | 0 |
| L\W Ratio | 1 | 1.4 |
| Efficiency | 1.4 | 1.6 |
| Culet Size | 0 | 0 |
| Sec. Crown Angle | 30 | 33 |
| Crown Division Point | 50 | 50 |
| Sec. Pavilion Angle | 58 | 64 |
| Pavilion Division Point | 34 | 40 |
| Pavilion Corner Angle | 50 | 54 |
| Pavilion Corner Ratio | 8 | 12 |

TABLE 4

Relative Reference Rectangle Dimensions (top view)

| Parameter | From | To |
|---|---|---|
| Girdle Thickness (M) | 2 | 4.5 |
| Table size | 55 | 63 |
| Total Depth | 62 | 72 |
| Natural Cult |  | 0 |
| Natural Diameter |  | 0 |
| Culet Off-Center Width | 0 | 0 |
| Culet Off-Center Length | 0 | 0 |
| Table Off-Center Width | 0 | 0 |
| Table Off-Center Length | 0 | 0 |
| L\W Ratio | 1 | 1.05 |
| Efficiency | 140 | 160 |
| Culet Size | 0 | 0 |
| Pavilion Angle 1 | 48 | 55 |
| Pavilion Angle 2 | 41 | 43 |
| Pavilion Angle 3 | 28 | 32 |
| Pavilion Depth 1 | 43 | 47 |
| Pavilion Depth 2 | 75 | 80 |
| Crown Angle 1 | 45 | 50 |
| Crown Angle 2 | 40 | 44 |
| Crown Angle 3 | 28 | 35 |
| Crown Height 1 | 45 | 48 |
| Crown Height 2 | 73 | 77 |

TABLE 5

Relative Reference Princess Dimensions (top view)

| Parameter | From | To |
|---|---|---|
| Girdle Thickness (M) | 2.4 | 4 |
| Table size | 62 | 73 |
| Crown Angle | 38 | 42 |
| Pavilion Angle | 39 | 42 |
| Crown Height | 6 | 12 |
| Total Depth | 62 | 73 |
| Natural Culet |  | 0 |
| Natural Diameter |  | 0 |
| Culet Off-Center Width | 0 | 0 |
| Culet Off-Center Length | 0 | 0 |
| Table Off-Center Width | 0 | 0 |
| Table Off-Center Length | 0 | 0 |
| L\W Ratio | 1 | 1.05 |
| Culet Size | 0 | 0 |
| Crown Width Ratio | 1 | 99 |
| Crown Height Ratio | 50 | 50 |
| Crown Second Angle | 20 | 40 |
| Crown Angles Difference | 5 | 8 |
| Pavilion Width Ratio | 1 | 99 |
| Pavilion Division Point | 35 | 75 |
| Sec. Pavilion Angle | 35 | 75 |
| Pavil. Height Div. Max. Diff. |  | 100 |
| Pavilion Max Variation |  | 4 |

TABLE 6

Relative Reference Marquise Dimensions (top view)

| Parameter | From | To |
|---|---|---|
| Girdle Thickness (M) | 2.4 | 4 |
| Table size | 55 | 62 |
| Crown Angle | 32 | 36 |
| Pavilion Angle | 40 | 42 |
| Total Depth | 58 | 63 |
| Natural Culet |  | 0 |
| Natural Diameter |  | 0 |
| Culet Off-Center Width | 0 | 0 |
| Culet Off-Center Length | 0 | 0 |
| Table Off-Center Width | 0 | 0 |
| Table Off-Center Length | 0 | 0 |
| L\W Ratio | 1.7 | 2.3 |
| Girdle Bending | 50 | 50 |
| Culet Size | 0 | 0 |

TABLE 7

Relative Reference S. French Marquise Dimensions (top view)

| Parameter | From | To |
|---|---|---|
| Girdle Thickness (M) | 2.4 | 4 |
| Table size | 55 | 63 |
| Crown Angle | 32 | 36 |
| Pavilion Angle | 40 | 42 |
| Total Depth | 58 | 63 |

TABLE 7-continued

Relative Reference S. French Marquise Dimensions (top view)

| Parameter | From | To |
|---|---|---|
| Natural Culet |  | 0 |
| Natural Diameter |  | 0 |
| Culet Off-Center Width | 0 | 0 |
| Culet Off-Center Length | 0 | 0 |
| Table Off-Center Width | 0 | 0 |
| Table Off-Center Length | 0 | 0 |
| L\W Ratio | 1.7 | 2.5 |
| Girdle Bending | 50 | 50 |
| Culet Size | 0 | 0 |

TABLE 8

Relative Reference Oval Dimensions (top view)

| Parameter | From | To |
|---|---|---|
| Girdle Thickness (M) | 2.4 | 4 |
| Table size | 55 | 62 |
| Crown Angle | 32 | 36 |
| Pavilion Angle | 40 | 42 |
| Crown Height | 12 | 16 |
| Total Depth | 57 | 63 |
| Natural Culet |  | 0 |
| Natural Diameter |  | 0 |
| Culet Off-Center Width | 0 | 0 |
| Culet Off-Center Length | 0 | 0 |
| Table Off-Center Width | 0 | 0 |
| Table Off-Center Length | 0 | 0 |
| L\W Ratio | 1.3 | 1.55 |
| Efficiency | 77 | 83 |
| Culet Size | 0 | 0 |

TABLE 9

Relative Reference Cushion Brilliant Dimensions (top view)

| Parameter | From | To |
|---|---|---|
| Girdle Thickness (M) | 2.4 | 4 |
| Table size | 62 | 73 |
| Crown Angle | 32 | 36 |
| Pavilion Angle | 36 | 40 |
| Crown Height | 12 | 15 |
| Total Depth | 62 | 73 |
| Natural Culet |  | 0 |
| Natural Diameter |  | 0 |
| Culet Off-Center Width | 0 | 0 |
| Culet Off-Center Length | 0 | 0 |
| Table Off-Center Width 1K | 0 | 0 |
| Table Off-Center Length | 0 | 0 |
| L\W Ratio | 1 | 1.2 |
| Efficiency | 60 | 70 |
| Culet Size | 0 | 0 |
| Pavilion First Angle | 56 | 60 |
| Pavilion First Height | 35 | 45 |
| Pavilion First Corner Height | 30 | 40 |
| Pavilion First Corner Angle | 58 | 58 |
| Pavilion Upper Height | 90 | 90 |

TABLE 10

Relative Reference Pear Dimensions (top view)

| Parameter | From | To |
|---|---|---|
| Girdle Thickness (M) | 2.4 | 5 |
| Table size |  | 60 |
| Crown Angle | 33 | 37 |
| Pavilion Angle | 38 | 41.7 |
| Crown Height | 12 | 15 |
| Pavilion Depth | 39 | 44 |
| Total Depth | 59 | 63 |
| Natural Culet |  | 0 |
| Natural Diameter |  | 0 |
| Culet Off-Center Width | 0 | 0 |
| Culet Off-Center Length | 0 | 0 |
| Table Off-Center Width | 0 | 0 |
| Table Off-Center Length | 0 | 0 |
| L\W Ratio | 1.4 | 1.6 |
| Girdle Bending | 50 | 50 |
| Culet Size | 0 | 0 |

TABLE 11

Relative Reference Pearmirage Dimensions (top view)

| Parameter | From | To |
|---|---|---|
| Girdle Thickness (M) | 2.4 | 4 |
| Table size | 55 | 63 |
| Crown Angle | 32 | 36 |
| Pavilion Angle | 38 | 42 |
| Crown Height |  | 16 |
| Total Depth | 58 | 63 |
| Natural Culet |  | 0 |
| Natural Diameter |  | 0 |
| Culet Off-Center Width | 0 | 0 |
| Culet Off-Center Length | 0 | 0 |
| Table Off-Center Width | 0 | 0 |
| Table Off-Center Length | 0 | 0 |
| L\W Ratio | 1.4 | 1.6 |
| Girdle Bending |  | 55 |
| Culet Size | 0 | 0 |

TABLE 12

Relative Reference French Pearmirage Dimensions (top view)

| Parameter | From | To |
|---|---|---|
| Girdle Thickness (M) | 2.4 | 4 |
| Table size | 55 | 63 |
| Crown Angle | 32 | 36 |
| Pavilion Angle | 39 | 42 |
| Total Depth | 57 | 63 |
| Natural Culet |  | 0 |

TABLE 12-continued

Relative Reference French Pearmirage Dimensions (top view)

| Parameter | From | To |
|---|---|---|
| Natural Diameter | | 0 |
| Culet Off-Center Width | 0 | 0 |
| Culet Off-Center Length | 0 | 7 |
| Table Off-Center Width | 0 | 0 |
| Table Off-Center Length | 0 | 0 |
| L\W Ratio | 1.4 | 1.6 |
| Girdle Bending | | 60 |
| Culet Size | 0 | 0 |

TABLE 13

Relative Reference French Pear Dimensions (top view)

| Parameter | From | To |
|---|---|---|
| Girdle Thickness (M) | 2.4 | 4 |
| Table size | 55 | 63 |
| Crown Angle | 32 | 36 |
| Pavilion Angle | 39 | 42 |
| Total Depth | 57 | 63 |
| Natural Culet | | 0 |
| Natural Diameter | | 0 |
| Culet Off-Center Width | 0 | 0 |
| Culet Off-Center Length | 0 | 74 |
| Table Off-Center Width | 0 | 0 |
| Table Off-Center Length | 0 | 0 |
| L\W Ratio | 1.4 | 1.6 |
| Girdle Bending | | 60 |
| Culet Size | 0 | 0 |

TABLE 14

Relative Reference French Marquiz Dimensions (top view)

| Parameter | From | To |
|---|---|---|
| Girdle Thickness (M) | 2.4 | 4 |
| Table size | 55 | 62 |
| Crown Angle | 32 | 36 |
| Pavilion Angle | 39 | 42 |
| Total Depth | 57 | 63 |
| Natural Culet | | 0 |
| Natural Diameter | | 0 |
| Culet Off-Center Width | 0 | 0 |
| Culet Off-Center Length | 0 | 0 |
| Table Off-Center Width | 0 | 0 |
| Table Off-Center Length | 0 | 0 |
| L\W Ratio | 1.7 | 2.3 |
| Girdle Bending | 50 | 50 |
| Culet Size | 0 | 0 |

It will be understood that the reference shapes and relative dimensions disclosed herein are only exemplary and the methods described herein allow for significant variation from the shapes provided in the figures and the values provided in the foregoing tables, such as differences in shape types or variations of particular aspects of a shape type. In particular examples the variations in shape include variations in dimensions within a shape type of between 0%-1%, about 1%, about 2%, about 3%, about 4%, about 5%, 5-10%, 10-15%, 15-20%, 20-25%, 25-30% or greater. For example, the illustrative reference shapes presented in FIGS. 3-12 have relative dimensions shown in the following Table 15. In the following table, "Table %" and "Total Depth %" are determined as described above. Additionally shown is the ratio between the table width and table length.

TABLE 15

Figure Shapes Dimensions

| Shape | Ratio (W:H) | Table % | Total Depth % |
|---|---|---|---|
| Marquise | 1:2 | 56-63 | 59.2-62.4 |
| Emerald | 1:1.4 | 65-68 | 65 |
| Square Emerald | 1:1 | 65-67 | 65 |
| Asher | 1:1 | 65-68 | 65 |
| Heart | 1:1.35 | 64-72 | 63-67 |
| Oval | 1:1.5 | 56-63 | 59.2-62.4 |
| Pear | 1:1.6 | 56-63 | 59.2-62.8 |
| Princess | 1:1 | 70-73 | 70-72 |
| Radiant | 1:1 | 65-70 | 69 |
| Cushion | 1:1 | 65-70 | 69 |

Relative dimensions of the "Round" gem depicted in FIG. 12, are shown in Table 16:

TABLE 16

Relative Dimensions of "Round" Shape (W:H = 1:1)

| Parameter | From | To |
|---|---|---|
| Table % | 53 | 62 |
| Total Depth % | 58.6 | 62.7 |
| Crown Angle | 33 | 35 |
| Pavilion Angle | 41 | 41.2 |
| Crown Height | 12.3 | 16.5 |
| Pavilion Depth | 43.2 | 43.6 |

In the exemplary embodiment shown in FIG. 2, a user first obtains a test gem image (110), and then accesses a desired reference shape image (120) from a database of shapes. It is appreciated that the order of the foregoing is not crucial and can be reversed. Additionally, in some embodiments, the user accesses multiple references shape images for use in comparison of the test gem image. In such embodiments, comparison to multiple images can proceed in parallel or one after the other, following the same procedure described herein. Once a test gem image is obtained and the reference shape image is accessed, the processor (10, FIG. 1) begins the comparison between the test gem shape and reference shape by overlaying the test gem shape and the reference shape (130, FIG. 2). In particular embodiments, overlaying the test and reference shapes (130) is a "virtual" overlaying or comparison of the digital data representing the two shapes. In other examples, the overlaying step is not virtual, but is displayed on the display (30, FIG. 1) as two overlaid images (not shown). One of skill will appreciate that the size and orientation of the reference shape and the test shape may not be comparable (e.g. too big, too small, positioned at an angle, and the like). In such instances, the size and orientation of the reference shape are adjusted as needed to best match the size and orientation of the test image (140). Adjustment of the reference shape can include, but is not limited to size adjustments (expansion/contraction) and rotational axis adjustments. Methods of image adjustment are standard in the art of digital imaging. In particular examples, a user can manually manipulate the orientation and size of the reference shape image to best match the orientation and size of the test shape. In other examples, the computer is programmed to manipulate the reference shape image (or the data representative thereof) to adjust the reference shape image (or data) orientation and size to best fit the test gem image orientation and size.

After the reference shape is adjusted (140), the two shapes (reference shape and test shape) are aligned to the extent possible, and the processor (10, FIG. 1) calculates the non-overlapping area between the two shapes (150). In particular embodiments, a user manually aligns the two shapes. In other embodiments, the shapes are aligned by the processor (10, FIG. 1) (processor-alignment can be either virtual or shown on the display (20, FIG. 1)). Any method of area calculation known in the art can be used to calculate the non-overlapping area (see for examples Jurgensen et al.). In particular embodiments, it is the entirety of the test shape that is aligned with the reference shape. In other embodiments, it is only one or more particular aspect(s) of the test shape that is aligned, for example, but not limited to, the curvature of a face, the intersection of points between particular individual facets, or the entirety of a particular facet or face of the shapes being compared. Likewise, in some embodiments, the area of the entire shape is compared, while in others the area of only particular aspects of the reference and test shapes are compared.

The correspondence between the test shape and the reference shape is measured as the percent of the test shape area that is non-overlapping with the reference shape. In one embodiment, the non-overlapping area between the test and reference shapes is calculated first (150), followed by the area of the test shape, and then the non-overlapping percent is determined (160). As before, any method of determining area known to the art can be used to determine the test shape area. It will be appreciated however, that there is no requirement to determine the test shape area at this particular stage of the process described in FIG. 2. Test shape area can be calculated at any stage of the process up until it is needed for the determination of percent non-overlapping area (160); for example, the test shape area can be calculated when the test shape image is obtained (110).

After the percent non-overlapping area is determined (160), the processor (10, FIG. 1) determines a shape grade relative to the calculated percent non-overlapping area (170). Shape grade can be any type of relative gemstone grade known in the art (e.g. letter, number, range from Excellent to Poor, and the like). Additionally, shape grading can be more or less stringent, depending on non-limiting factors such as which test shape is being evaluated. Grading stringency is reflected in the allowable percent non-overlapping area between shape grade levels. For example in a more stringent grading system, shape grade can change with every 0-3% non-overlapping area. In a less stringent grading system, shape grade can change with every 5-10% non-overlapping area. One of skill will appreciate that any range (for example, 1-3%, 0.5-4%, 2-6%, 8-12%, and the like) can be used as the criteria to distinguish between shape grades. It will also be appreciated that within the same grading system, different grades can be more stringent than others. For example, in some examples, differences between the highest and second-highest grade can allow for only a small non-overlapping area (e.g. 1-2%), whereas differences between the second and third-highest grades may be less stringent (e.g. 8-12%). In those embodiments wherein the test gem is compared to multiple reference gem shapes, the final shape grade for the gem can be in relation to each reference shape or can be a combination of the separate grades.

Once a shape grade is determined (170), the grade is saved to memory (180) and the grade, along with the test and reference shape overlay comparison, is displayed on the display (190).

It will be appreciated that the foregoing is just one non-limiting example of the methods described herein. In particular embodiments, determining a shape grade requires evaluation of multiple (e.g. two, three, four) views of the test shape in comparison to its reference shape counterpart. In such embodiments, determining the shape grade relative to percent non-overlapping area (170) requires determination of the percent non-overlapping area for each view of the test shape. In particular examples, shape grade is determined by the average (e.g. mean) percent non-overlapping area between each view. In other examples, shape grade is determined by separate analysis of each view (e.g. allowable percent non-overlapping area for each of the evaluated views). In still further embodiments, shape grade is a function of a combination of the percent non-overlapping area of one or more views of a test gem and one or more aspects (facets, alignment of particular curves, and the like) of the test gem.

In still further embodiments, it is the percent overlapping area between one or more views/aspects of a test shape and a reference shape, which is used to determine a shape grade. In such embodiments, the procedures described above are followed, except it is the region of overlap used in the shape grading determination.

FIG. 2 describes an exemplary computer-implemented embodiment of the described method of evaluating a gemstone shape. It will be understood however, that several, if not all, aspects of the foregoing method do not require use of a computer, and fall within the scope of this disclosure. For example, in particular embodiments, "obtaining" a test gem image includes acquiring a test gem image by way of any imaging device, including use of a film camera. In other embodiments, obtaining test gem images includes processing of an already-acquired image (e.g. a paper, digital, or film image) for use in the described methods. In particular examples, a paper, film (e.g. film negatives or slides), or similar "hard copy" test gem image can be scanned into a computer for use in a computer-implemented method such as that shown in FIG. 1. In other examples, a previously-acquired test image and/or reference image (e.g. hard copy image) can be transferred to a film transparency which can then be overlaid on top each other.

V. Methods for Identifying Gemstone Shape

It is appreciated that it is not always possible to determine the shape of a cut or rough gemstone without further analysis. To address this problem, provided herein are methods for identifying a gemstone shape. In the described methods, the image of a test gem (containing a test gem shape) is obtained. The test gem shape is then compared with images of multiple different reference gem shapes; and the differences between the test gem shape and the reference gem shapes are determined, wherein the gem shape is identified as the reference gem shape having the fewest differences from the test gem shape.

Figure 13:
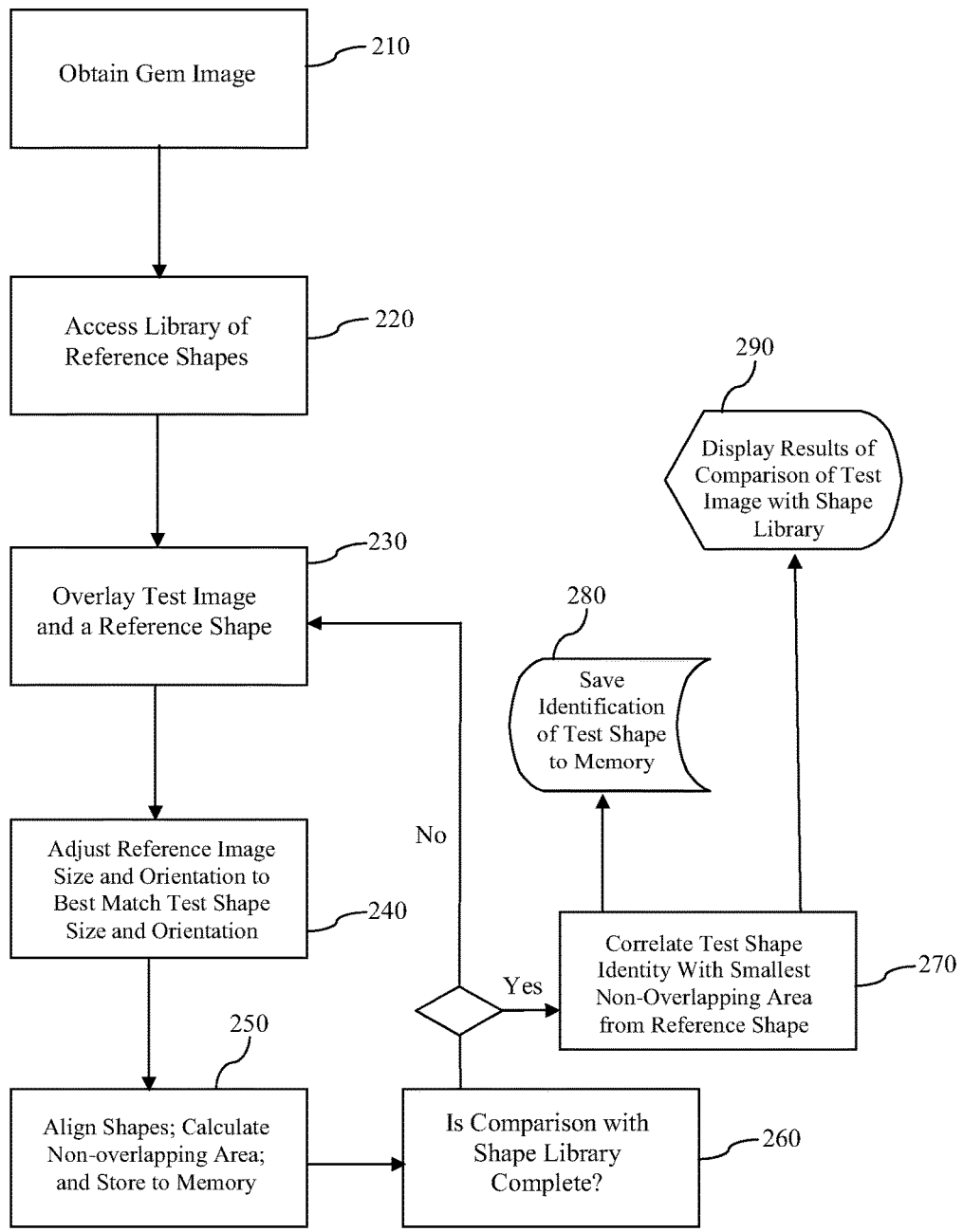
FIG. 13 is a process flow chart, showing an exemplary embodiment of the described method of identifying gemstone shape.

An exemplary, computer-implemented, embodiment of the described method of identifying a gemstone shape is set forth in FIG. 13. Similar to the method shown in FIG. 2, a computer system such as the system shown in FIG. 1 is suitable for performing the described method.

With reference to FIG. 13, the method begins with obtaining an image of a test gem (210) by any of the methods described above. The processor (e.g. 10, FIG. 1) then accesses from the computer memory (20, FIG. 1) a library of images of reference shapes (220). The reference shapes in the library can be rendered by any method described above, and can be selected from and have the dimensions of the shapes depicted in FIGS. 3-12, and as described in Tables 1-16, above. In particular embodiments, examples of the shapes that can be in the reference shapes library include, but are not limited to, Heart, Emerald, Radiant, Rectangle, Princess, Marquise, S. French Marquise, Oval, Cushion, Pear, Pearmirage, French Pearmirage, French Pear, French Marquiz, Round, Asscher, Trilliant, Octahedron, Sawable, Cleavage, Makable, Flat, Crystal, and Maacle.

The test shape (in the test image) is compared with one of the reference shapes in the accessed library by overlaying the two shapes (230) as described herein (130, FIG. 2). Also as described (140, FIG. 2) the size and orientation of the reference shape is adjusted to best match that of the test shape (240). Once adjusted, the shapes are aligned and the non-overlapping area is calculated (250) as discussed above (150, FIG. 2). The calculated area is also stored to memory (250).

Following calculation of the non-overlapping area (250), the processor (10, FIG. 1) determines if the comparison with the reference shape library is complete or if additional shapes in the reference shape library remain to be compared with the test shape (260). If the comparison is not complete, and additional shapes remain, then a remaining shape is compared with the test shape as above (230-250). If the comparison with the reference shape library is complete, the processor (10, FIG. 1), analyzes the calculated non-overlapping areas to determine which is smallest, and identifies the test shape as the shape from the library with which the test shape has the smallest non-overlapping area (270). The results of the shape identification are then saved (280) to computer memory (20, FIG. 1), and displayed (290) on the display (30, FIG. 1).

The following examples are provided to illustrate certain particular features and/or embodiments. These examples should not be construed to limit the disclosure to the particular features or embodiments described.

EXAMPLES

Example 1: Grading a Diamond Shape

This example illustrates use of the method described herein to grade the whole shape of a diamond.

A diamond to be sold as a "Cushion" shape is evaluated using the method outlined in FIG. 2.

A top-view image of the test "Cushion" diamond is obtained using a Sarin DIAMENSION® diamond grading machine, connected to a computer. The Sarin machine also calculates the area of the test "Cushion" image. Once acquired, the test image (and its calculated area) is stored in the computer memory and displayed on the computer display. A top view of a reference "Cushion" shape (as depicted in FIG. 4) is then accessed from the computer memory and overlaid on top of the displayed test image. In this example, the reference shape image is approximately half the size of the acquired test image. To compensate for this difference, the user selects the reference image shape with a mouse and expands the shape size to align it with the test shape. The computer then calculates (a) the non-overlapping area between the two shapes, and (b) the percent non-overlapping area (in relation to the test image area). The results of these calculations are displayed on the screen.

In this example, the criteria for the highest, or "Excellent" shape grade is if the percent non-overlapping area is 5% or less.

Example 2: Grading Cushion Diamond Facet

This example illustrates the application of the described method to compare a facet from a test "Cushion" diamond with that of a reference "Cushion" shape.

Grading a test diamond is carried out as illustrated in FIG. 2 and described in Example 1, except that only a facet of the acquired test gem image is compared to a facet of the reference Cushion shape. In this example, the central facet of the top-view of the test Cushion shape is compared with the corresponding central facet in the reference shape. One difference from the procedure described in Example 1, is that instead of adjusting the reference shape to be in alignment with the entire test shape, the reference shape is adjusted to align its central facet with that of the test shape. Likewise, only the non-overlapping area between the test and reference facets is calculated (and percent of the total area of the test shape facet), and used in the determination of shape grade.

Example 3: Identification of a Diamond Shape

This example describes the identification of a diamond shape.

Identification of a diamond shape can be achieved using the procedure illustrated in FIG. 13.

To identify the shape of a diamond, a test diamond of unidentifiable shape is imaged using a Sarin diamond grading machine. The obtained image is saved in the memory of a computer and compared to a library of images of reference shapes. Comparison of the test and reference shapes proceeds for each shape in the library by overlaying the shapes, adjusting the reference shape to match the size and orientation of the test shape, aligning the shapes, and calculating the non-overlapping area of the test and each reference shape in the image library. Calculated non-overlapping areas are compared, and the smallest non-overlapping area between test and reference shapes indicates the identity of the reference shape.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as our invention all that comes within the scope and spirit of these claims.

I claim:

1. A method for evaluating the fidelity of the shape of a test gem, comprising:
   obtaining a test gem image of the test gem, wherein the test gem image comprises a two-dimensional image or a three-dimensional image, wherein the test gem image comprises a test gem shape;
   obtaining at least one reference gem image comprising at least one reference gem shape; comparing the test gem image with the at least one reference gem image;
   determining differences between the test gem image and the at least one reference gem image;

overlaying the test gem image with the at least one reference gem image;

measuring a total percentage overlap between the test gem image and the at least one reference gem image;

displaying the test gem image and the at least one reference gem image on a display and overlaying the images; and assigning a shape grade to the test gem as a function of the determined differences and the measured percentage overlap, wherein the shape grade indicates the fidelity of the test gem shape to the at least one reference gem shape.

2. The method of claim 1, wherein the test gem shape and the at least one reference gem shapes are selected from the group consisting of Heart, Emerald, Radiant, Rectangle, Princess, Marquise, S. French Marquise, Oval, Cushion, Pear, Pearmirage, French Pearmirage, French Pear, French Marquiz, Round. Asscher, Trilliant, Octahedron, Sawable, Cleavage, Makable, Flat, Crystal, and Maacle, or a variation thereof.

3. The method of claim 1, wherein the comparing the test gem shape with the at least one reference gem shape comprises overlaying the test gem image and each of the at least one reference gem image.

4. The method of claim 3, wherein the determining differences between the test gem shape and the at least one reference gem shape comprises calculating the non-overlapping area between the overlaid images.

5. The method of claim 1, wherein the comparing the test gem shape with the at least one reference gem shape comprises comparing the shape of one or more facets of the test gem shape and the at least one reference gem shape.

6. The method of claim 1, wherein the comparing the test gem shape with the at least one reference gem shape comprises comparing the overall or partial curvature of the test gem shape with the at least one reference gem shape.

7. The method of claim 1, wherein prior to determining differences between the test gem shape and the at least one reference gem shape, the reference gem image of the at least one reference gem shape is adjusted to a size comparable to that of the test gem shape.

8. The method of claim 1, further comprising measuring the dimensions of the test gem shape prior to comparing the test gem shape with the at least one reference gem shape.

9. The method of claim 1, wherein the test gem comprises a diamond, ruby, emerald, or sapphire.

10. A computer-implemented method for evaluating a gem shape, comprising:

obtaining a test gem image of a test gem with a camera connected to a computer, wherein the test gem image comprises a test gem shape;

accessing from the computer memory, at least one reference gem image comprising at least one reference gem shape;

comparing the test gem shape with the at least one reference gem shape, wherein the comparing the test gem shape with the at least one reference gem shape comprises displaying the test gem shape image and the reference gem shape image on a display and overlaying the images;

determining differences between the test gem image and the at least one reference gem image;

measuring a total percentage overlap between the test gem image and the at least one reference gem image;

displaying the differences between the test gem image and the at least one reference gem image on the display; and assigning a shape grade to the test gem as a function of the determined differences and the measured percentage overlap, wherein the shape grade indicates the fidelity of the test gem shape to the at least one reference gem shape.

11. The method of claim 10, wherein prior to the determining differences between the test gem image and the at least one reference gem image, the at least one reference gem image is adjusted to a size comparable to that of the test gem image.

12. The method of claim 10, wherein the test gem comprises a diamond, ruby, emerald, or sapphire.

13. A computer-implemented method for evaluating a gem shape, comprising:

obtaining a test gem image of a test gem with a camera connected to a computer, wherein the test gem image comprises a test gem shape;

accessing from the computer memory, at least one reference gem image comprising at least one reference gem shape;

comparing the test gem shape with the reference gem shape, the comparing the test gem shape with the at least one reference gem shape comprising displaying the test gem image and the at least one reference gem image on a display and overlaying the images;

determining similarities between the test gem image and the reference gem image;

measuring a total percentage overlap between the test gem image and the at least one reference gem image;

displaying the similarities between the test gem image and the reference gem image on the display; and assigning a shape grade to the test gem as a function of the determined similarities and the measured percentage overlap, wherein the shape grade indicates the fidelity of the test gem shape to the at least one reference gem shape.

14. A method for identifying a gem shape of a test gem, comprising:

obtaining a test gem image of the test gem;

obtaining multiple reference gem images comprising corresponding multiple reference gem shapes;

comparing the test gem image with the multiple reference gem images, the comparing the test gem image with the multiple reference gem images comprising displaying the test gem image and each of the multiple reference gem images on a display and overlaying the test gem image and each of the multiple reference gem images; and determining the differences between the test gem image and each of the multiple reference gem images;

measuring a total percentage overlap between the test gem image and the at least one reference gem image; and identifying a test gem shape as the reference gem shape corresponding to the reference gem image having the fewest differences from the test gem shape and based in part on the measured percentage overlap.

15. A method for identifying a gem shape of a test gem, comprising:

obtaining a test gem image of the test gem;

obtaining multiple reference gem images comprising corresponding multiple reference gem shapes;

comparing the test gem image with the multiple reference gem images, the comparing the test gem image with the multiple reference gem images comprising displaying the test gem image and each of the multiple reference gem images on a display and overlaying the test gem image and each of the multiple reference gem images;

determining the similarities between the test gem image and each of the multiple reference, gem images;

measuring a total percentage overlap between the test gem image and the at least one reference gem image; and identifying a test gem shape as the reference gem shape corresponding to the reference gem image having the most similarities to the test gem image and based in part on the measured percentage overlap.

16. The method of claim 10, wherein the test gem shape and the at least one reference gem shape are selected from the group consisting of Heart, Emerald, Radiant, Rectangle, Princess, Marquise, S. French Marquise, Oval, Cushion, Pear, Pearmirage, French Pearmirage, French Pear, French Marquiz, Round. Asscher, Trilliant, Octahedron, Sawable, Cleavage, Makable, Flat, Crystal, and Maacle, or a variation thereof.

* * * * *